United States Patent
Tatara et al.

(10) Patent No.: US 12,402,790 B2
(45) Date of Patent: Sep. 2, 2025

(54) OPHTHALMIC APPARATUS, METHOD OF CONTROLLING THE SAME, AND RECORDING MEDIUM

(71) Applicant: TOPCON CORPORATION, Tokyo (JP)

(72) Inventors: Yoko Tatara, Kita-ku (JP); Tatsuo Yamaguchi, Warabi (JP); Makoto Saika, Nerima-ku (JP)

(73) Assignee: TOPCON CORPORATION, Tokyo (JP)

( * ) Notice: Subject to any disclaimer, the term of this patent is extended or adjusted under 35 U.S.C. 154(b) by 1276 days.

(21) Appl. No.: 16/935,217

(22) Filed: Jul. 22, 2020

(65) Prior Publication Data

US 2021/0038071 A1 Feb. 11, 2021

(30) Foreign Application Priority Data

Aug. 8, 2019 (JP) .................................. 2019-145923

(51) Int. Cl.
*A61B 3/10* (2006.01)
*A61B 3/00* (2006.01)
(Continued)

(52) U.S. Cl.
CPC ............ *A61B 3/102* (2013.01); *A61B 3/0041* (2013.01); *A61B 3/1225* (2013.01);
(Continued)

(58) Field of Classification Search
CPC .............................. A61B 3/102; A61B 3/0041
(Continued)

(56) References Cited

U.S. PATENT DOCUMENTS 10,314,480 B2 * 6/2019 Ishiai ........................ A61B 3/14
10,327,632 B2 * 6/2019 Horn ........................ G06T 3/047
(Continued)

FOREIGN PATENT DOCUMENTS

JP    2008-206684 A    9/2008
JP    2013-248376 A    12/2013
(Continued)

OTHER PUBLICATIONS

Atchison, D. A., et al., "Shape of the Retinal Surface in Emmetropia and Myopia," Investigative Ophthalmology & Visual Science, vol. 46, No. 8, Aug. 2005, pp. 2689-2707.
(Continued)

*Primary Examiner* — Zachary W Wilkes
(74) *Attorney, Agent, or Firm* — XSENSUS LLP

(57) ABSTRACT

An ophthalmic apparatus of an aspect example applies optical coherence tomography (OCT) to an eye, and includes an interferometer, an OCT data generating unit, an optical path length changing unit, and a processing unit. The interferometer includes a measurement arm and a reference arm. The OCT data generating unit is configured to generate OCT data based on an output from the interferometer. The optical path length changing unit is configured to change at least one of the optical path length of the measurement arm and the optical path length of the reference arm. The processing unit is configured to control the optical path length changing unit to place partial data of the OCT data corresponding to a predetermined part of the eye at a standard depth level. The standard depth level is set based on a predetermined ocular parameter value.

26 Claims, 19 Drawing Sheets

(51) Int. Cl.
*A61B 3/12* (2006.01)
*G06T 7/00* (2017.01)
*G06T 11/00* (2006.01)

(52) U.S. Cl.
CPC .......... *G06T 7/0012* (2013.01); *G06T 11/008* (2013.01); *G06T 2207/10101* (2013.01); *G06T 2207/30041* (2013.01)

(58) Field of Classification Search
USPC .................................................. 351/206, 246
See application file for complete search history.

(56) References Cited

U.S. PATENT DOCUMENTS

| | | | |
|---|---|---|---|
| 2008/0204655 A1 | 8/2008 | Kikawa et al. | |
| 2012/0140179 A1* | 6/2012 | Miyasa .................. | A61B 3/102 351/246 |
| 2014/0128731 A1 | 5/2014 | Gonzalez et al. | |
| 2014/0333895 A1 | 11/2014 | Satake | |
| 2015/0042951 A1* | 2/2015 | Stanga ..................... | A61B 3/12 351/206 |
| 2015/0085252 A1 | 3/2015 | Fujimura et al. | |
| 2015/0305617 A1 | 10/2015 | Tachikawa et al. | |
| 2016/0345822 A1 | 12/2016 | Fujimura et al. | |
| 2017/0215725 A1* | 8/2017 | Ishiai ..................... | A61B 3/152 |
| 2018/0168445 A1* | 6/2018 | Horn ..................... | G06T 1/0007 |

FOREIGN PATENT DOCUMENTS

| | | |
|---|---|---|
| JP | 2014-073207 A | 4/2014 |
| JP | 2015-016151 A | 1/2015 |
| JP | 2015-208574 A | 11/2015 |
| JP | 2016-041221 A | 3/2016 |
| JP | 2017-086311 A | 5/2017 |
| JP | 2017-192828 A | 10/2017 |
| WO | 2013/002332 A1 | 1/2013 |

OTHER PUBLICATIONS

Bennett, A. G., et al., "Improvements on Littmann's method of determining the size of retinal features by fundus photography," Graefe's Arch Clin Exp Ophthalmol, 1994, pp. 232:361-367.

Office Action issued Mar. 28, 2023 in Japanese Patent Application No. 2019-145923 and English translation thereof, 8 pages.

Office Action issued Mar. 30, 2023 in European Patent Application No. 20189360.9 , 4 pages.

* cited by examiner

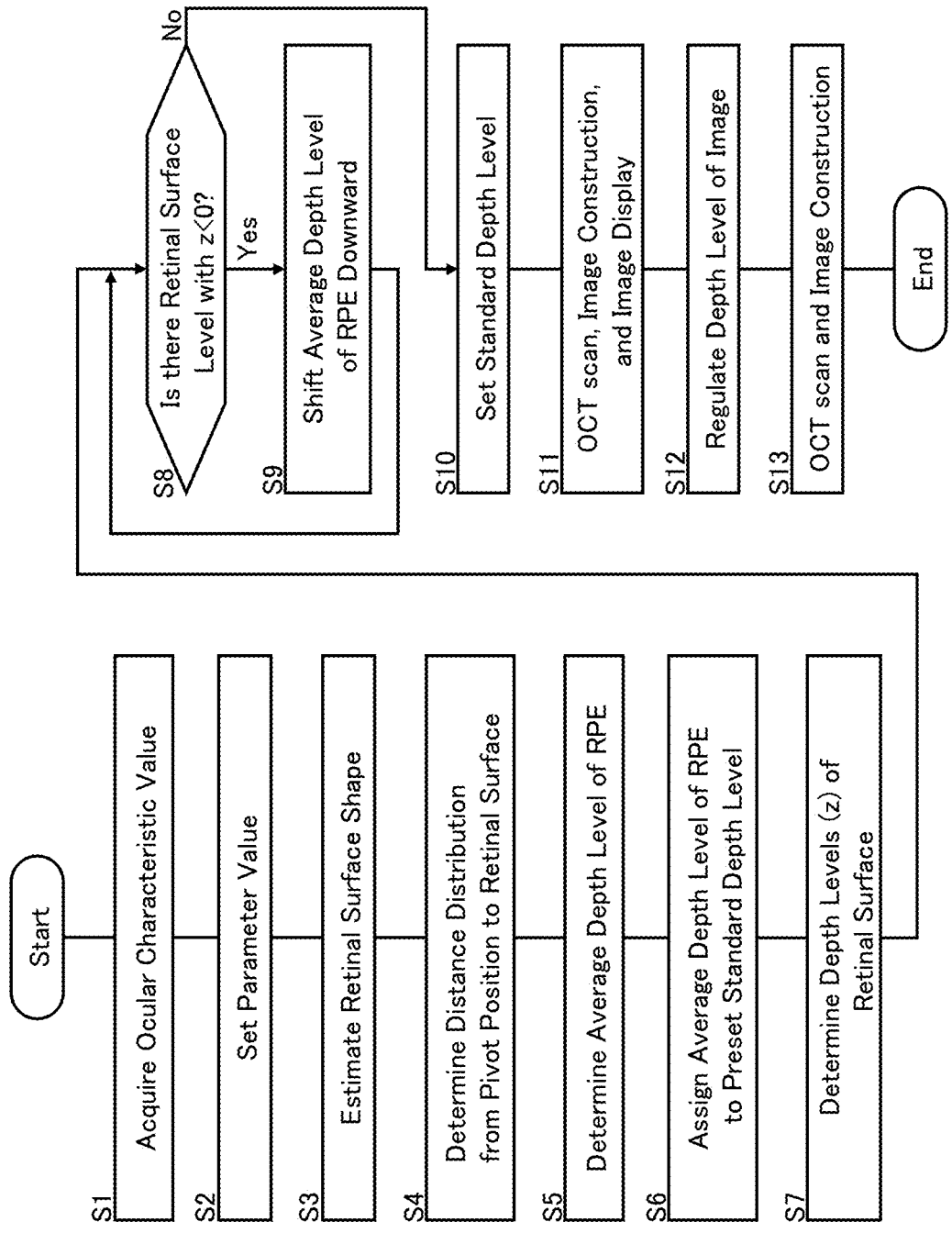

OPHTHALMIC APPARATUS, METHOD OF CONTROLLING THE SAME, AND RECORDING MEDIUM

CROSS-REFERENCE TO RELATED APPLICATION

The present application is based upon and claims the benefit of priority from Japanese Patent Application No. 2019-145923, filed Aug. 8, 2019; the entire contents of which are incorporated herein by reference.

FIELD

The present disclosure relates generally to an ophthalmic apparatus, a control method of an ophthalmic apparatus, and a recording medium.

BACKGROUND

Diagnostic imaging serves an important role in the field of ophthalmology. While a fundus camera, a scanning laser ophthalmoscope (SLO), and a slit lamp microscope have been conventionally used for ophthalmic diagnostic imaging, utilization of optical coherence tomography (OCT) has advanced in recent years.

OCT is generally an imaging technique for reconstructing a high-resolution image by taking out a signal from the inside of optical scattering media (e.g., biological tissue) using optical interference. An OCT apparatus includes an interferometer having a measurement arm and a reference arm, and further includes a mechanism for varying any one or both of the measurement arm length and the reference arm length in order to change the depth range to be imaged.

Furthermore, some ophthalmic apparatuses with an OCT function have an arm length adjustment function (an optical path length adjustment function) to cope with eye movement, pulsation and body motion. Known examples of such an optical path length adjusting function include Auto-Z and Z-lock. Auto-Z is an automatic operation for searching for an appropriate optical path length. Z-lock is an automatic operation for maintaining a state achieved by the Auto-Z (for example, see Japanese Unexamined Patent Application Publication No. 2016-41221). Typically, Auto-Z performs optical path length control such that a predetermined reference site of the subject's eye is depicted and located at a predetermined standard depth level in the image frame, and Z-lock, which follows the Auto-Z, performs optical path length control such that the state in which the reference site is depicted and located at the standard depth level is maintained.

For conventional ophthalmic apparatuses having an OCT function, a standard depth level, which is a targeted depiction location of a reference site, has been fixed. However, there are individual differences in the sizes and shapes of eyes, and, for example, when the axial length of the subject's eye is relatively long (e.g., when the subject's eye has myopia), an image protruding from the upper edge of the image frame is folded over and depicted in the image frame (for example, see Japanese Unexamined Patent Application Publication No. 2014-73207 and Japanese Unexamined Patent Application Publication No. 2017-86311).

Note that it is also possible to conduct a measurement for setting a standard depth level in accordance with individual differences of eyes, before the optical path length adjustment. However, so doing may newly create problems such as making the time required for examination longer, and making the burden on the subject heavier.

SUMMARY

One object of the ophthalmic apparatus, the control method of the same, and the recording medium according to the present disclosure is to improve the optical path length adjusting function of OCT.

The first aspect example is an ophthalmic apparatus that applies optical coherence tomography (OCT) to an eye, and includes an interferometer, an OCT data generating unit, an optical path length changing unit, and a processing unit. The interferometer includes a measurement arm and a reference arm. The OCT data generating unit is configured to generate OCT data based on an output from the interferometer. The optical path length changing unit is configured to change at least one of the optical path length of the measurement arm and the optical path length of the reference arm. The processing unit is configured to control the optical path length changing unit to place partial data of the OCT data corresponding to a predetermined part of the eye at a standard depth level. The standard depth level is set based on a predetermined ocular parameter value.

In the first aspect example, the standard depth level may be set such that an edge of first partial data corresponding to a predetermined first eye fundus tissue is placed on a lateral side of a frame.

In the first aspect example, the first eye fundus tissue may be a retinal surface. In addition, the standard depth level may be set based on second partial data corresponding to a predetermined second eye fundus tissue located at a deeper level than the retinal surface.

In the first aspect example, the standard depth level may be set at an average depth level of the second partial data or a deeper level.

In the first aspect example, the second eye fundus tissue may be a retinal pigment epithelium.

In the first aspect example, the second partial data corresponding to the retinal pigment epithelium may be set at a level deeper than the first partial data corresponding to the retinal surface by a predetermined distance.

In the first aspect example may further include an acquiring unit configured to acquire an ocular characteristic value of the eye. In addition, the processing unit may perform control of the optical path length changing unit for placing the partial data at the standard depth level, based on the ocular characteristic value.

In the first aspect example, the processing unit may perform the control such that an edge of third partial data corresponding to a predetermined third eye fundus tissue is placed on a lateral side of a frame.

In the first aspect example, the processing unit may perform the control based on fourth partial data corresponding to a predetermined fourth eye fundus tissue located at a deeper level than the third eye fundus tissue.

In the first aspect example, the processing unit may include a calculating processor configured to calculate an average depth level of the fourth partial data based on the ocular characteristic value, and may perform first control of the optical path length changing unit based on the average depth level and the standard depth level.

In the first aspect example, the processing unit may perform the first control such that the average depth level is placed at the standard depth level.

In the first aspect example, the processing unit may further include a judging processor configured to judge whether the edge of the third partial data is located on the lateral side.

In the first aspect example, the processing unit performs second control of the optical path length changing unit such that the average depth level is placed at a level deeper than the standard depth level if the judging processor judges that the edge is not located on the lateral side after the first control.

In the first aspect example, the judging processor may perform re-judgment after the second control.

In the first aspect example, the processing unit may repeat control of the optical path length changing unit for shifting the average depth level to a deeper level until the judging processor judges that the edge is located on the lateral side.

In the first aspect example, the judging processor may set the third partial data to a level shallower than the fourth partial data by a predetermined distance.

In the first aspect example, the fourth eye fundus tissue may be a retinal pigment epithelium. In addition, the calculating processor may include a shape estimating processor configured to determine an estimate shape of the retinal pigment epithelium based on the ocular characteristic value, and may determine the average depth level based on the estimate shape.

In the first aspect example, the calculating processor may further include a distance calculating processor configured to determine a distance distribution between a pivot position of OCT scanning and the estimate shape, and may determine the average depth level based on the distance distribution.

In the first aspect example, the third eye fundus tissue may be a retinal surface.

In the first aspect example, the OCT data generating unit may generate OCT data based on an output from the interferometer acquired after the control of the optical path length changing unit. In addition, the processing unit may perform third control of the optical path length changing unit based on the OCT data.

In the first aspect example, the processing unit may analyze the OCT data for detecting a fold-over artifact, and may perform the third control if the fold-over artifact is detected.

In the first aspect example, the processing unit may analyze the OCT data for detecting a retinal surface image, and may perform the third control if an edge of the retinal surface image is located on an upper edge of a frame.

In the first aspect example may further include a display unit and an operation unit. In addition, the OCT data generating unit may generate OCT data based on an output from the interferometer acquired after the control of the optical path length changing unit. Furthermore, the processing unit may include a display controller configured to control the display unit to display an OCT image based on the OCT data, and may perform fourth control of the optical path length changing unit based on an output from the operation unit in response to an instruction from a user.

In the first aspect example, the processing unit may change the standard depth level according to a size of OCT scanning applied to the eye.

The second aspect example is a method of controlling an ophthalmic apparatus that applies OCT to an eye. The ophthalmic apparatus includes an interferometer, an optical path length changing unit, and a processor. The interferometer includes a measurement arm and a reference arm. The optical path length changing unit is configured to change at least one of an optical path length of the measurement arm and an optical path length of the reference arm. The method includes a process of controlling the processor to generate OCT data based on an output from the interferometer. In addition, the method includes a process of controlling the optical path length changing unit to place partial data of the OCT data corresponding to a predetermined part of the eye at a standard depth level set based on a predetermined ocular parameter value. Any elements optionally combinable with the first aspect example may be combined with the second aspect example.

The third aspect example is a program that causes a computer to execute the method of the second aspect example. Any elements optionally combinable with the first aspect example may be combined with the third aspect example.

The fourth aspect example is a computer-readable non-transitory recording medium storing the program of the third aspect example. Any elements optionally combinable with the first aspect example may be combined with the fourth aspect example.

According to some aspect examples, the optical path length adjusting function of OCT can be improved.

BRIEF DESCRIPTION OF THE DRAWINGS

FIG. 13 is a flowchart showing an example of the operation of the ophthalmic apparatus according to another embodiment example.

DETAILED DESCRIPTION

Figure 1:
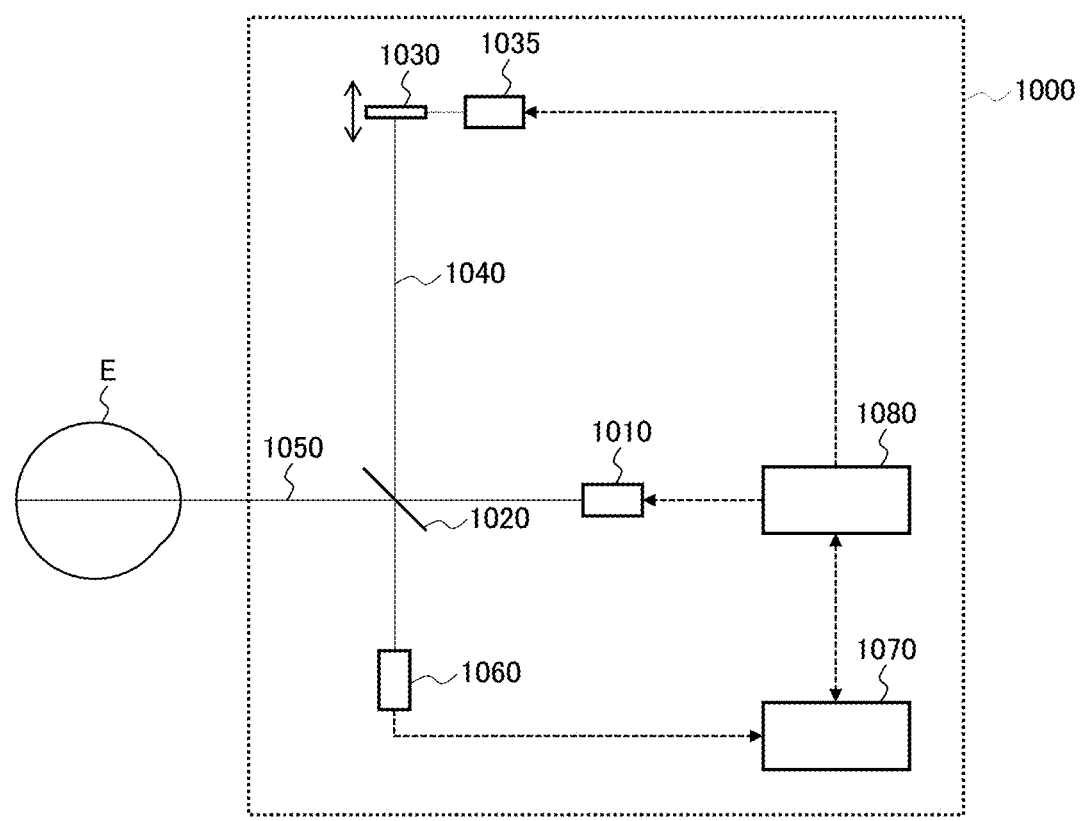
FIG. 1 is a schematic diagram showing an example of the configuration of the ophthalmic apparatus according to an aspect example.

Some aspect examples of embodiments of the present disclosure will be described in detail with reference to the drawings. The ophthalmic apparatus of some aspect examples is capable of applying optical coherence tomography (OCT) to the subject's eye, and also capable of adjusting the optical path length according to a standard depth level that has been set based on a predetermined ocular parameter value.

The ophthalmic apparatus of some aspect examples includes an interferometer, an OCT data generating unit, and an optical path length changing unit, like a typical, conventional ophthalmic OCT apparatus.

The interferometer includes a measurement arm and a reference arm. A typical interferometer is configured to perform the following actions: guiding the measurement light to the subject's eye with the measurement arm; guiding the return light of the measurement light from the subject's eye with the measurement arm; guiding the reference light with the reference arm; generating interference light by superposing the return light of the measurement light and the reference light with a beam combiner; and detecting the interference light with a photodetector.

The OCT data generating unit is configured to generate OCT data based on an output from the interferometer. A typical OCT data generating unit includes a processor that configured to operate according to an OCT data generation program. Typical OCT data is an intensity profile, or an image constructed by applying imaging process to the intensity profile. Here, the intensity profile is generated by applying at least Fourier transform to an interference signal output from the interferometer, and is at least an intensity distribution along the depth direction.

The optical path length changing unit is configured to change at least one of the optical path length of the measurement arm and the optical path length of the reference arm. A typical optical path length changing unit changes either one of the optical path length of the measurement arm and the optical path length of the reference arm. A typical optical path length changing unit applied to the measurement arm includes a corner cube provided in the middle of the measurement arm, a mechanism for moving the corner cube, and an actuator that applies a driving force to the mechanism. A typical optical path length changing unit applied to the reference arm includes a reflection mirror provided at the far end of the reference arm, a mechanism for moving the reflection mirror, and an actuator for applying a driving force to the mechanism. In another example, the optical path length changing unit applied to the reference arm may have the same configurations as those of the optical path length changing unit applied to the measurement arm described above.

The ophthalmic apparatus of some aspect examples further includes a processing unit. The processing unit is configured and programmed to control the optical path length changing unit to place partial data of the OCT data corresponding to a predetermined part of the eye at a standard depth level that has been set based on a predetermined ocular parameter value. A typical processing unit includes a processor that operates according to an optical path length control program. The ocular parameter value used for setting the standard depth level may include, for example, at least one of the axial length and the optical power. The setting of the standard depth level will be described later in more detail.

The standard depth level is the depth level or depth position (z coordinate) that is a targeted depiction level (or, targeted depiction position or targeted depiction depth) of a reference site (a predetermined part or tissue or site of an eye) of the subject's eye. When an OCT scan is applied to the eye fundus, an exemplary standard depth level may be set such that both edges or ends of a predetermined first eye fundus tissue are not cut off. In other words, the exemplary standard depth level may be set such that an edge of first partial data corresponding to the first eye fundus tissue is placed on a lateral side of a frame.

An exemplary first eye fundus tissue may be a retinal surface. In such cases, for example, a B-scan image (or a three dimensional image) of the fundus is constructed. The image region corresponding to the retinal surface (i.e., the inner limiting membrane, or ILM) typically has a convex shape toward the lower edge or bottom edge or base (the edge on the deep side) of the image frame, and the edge of the image region (e.g., the left edge and the right edge of such an image region in the B-scan image, or the peripheral edges of such an image region in the three dimensional image) is typically located nearest the upper edge of the image frame among all the points in the image region.

An exemplary standard depth level is set in such a manner that the edge of the image region corresponding to the retinal surface is placed on the lateral side (lateral edge) of the image frame. In other words, an exemplary standard depth level is set such that the image region intersects the lateral side of the image frame or such that the image region does not intersect the upper edge of the image frame.

Further, the exemplary standard depth level is set based on second partial data corresponding to a predetermined second eye fundus tissue located at a deeper level than the retinal surface. The second eye fundus tissue may be, for example, a site clearly depicted in OCT images, and may typically be a retinal pigment epithelium (RPE). For example, the standard depth level is set at an average depth level of the second partial data or a level deeper than the average depth level. The average depth level of the second partial data corresponding to the second eye fundus tissue is obtained, for example, as the average of the depth levels or depth positions (z coordinates) of a plurality of points (a plurality of pixels) that define the second partial data.

In the case where the second eye fundus tissue is the retinal pigment epithelium, the second partial data corresponding to the retinal pigment epithelium may be set at a level deeper than the first partial data corresponding to the retinal surface by a predetermined distance. A typical example of the predetermined distance is a standard value obtained in a clinical way, and is set to be 0.5 mm, for example. The same or a similar way may be applied when the first eye fundus tissue and/or the second eye fundus tissue are/is different from the above example. When the distance between the first partial data and the second partial data is set in advance like the above example, image analysis for detecting the second eye fundus tissue is not required, which leads to reducing resources and time required for OCT image analysis.

FIG. 1 shows one aspect of the ophthalmic apparatus as described above. The ophthalmic apparatus 1000 of the present aspect is used to apply OCT scanning to the subject's eye E. The type of the OCT technique is arbitrary and is typically Fourier domain OCT (spectral domain OCT or swept source OCT). The light source 1010, the photodetector 1060, the OCT data generating unit 1070, etc. have configurations according to the type of OCT adopted.

The light output from the light source 1010 is split by the beam splitter (also functioning as the beam combiner) 1020 into measurement light and reference light. In the present aspect, the light that has passed through the beam splitter 1020 is used as the measurement light while the light that has reflected by the beam splitter 1020 is used as the reference light; however, the other way around may also be adopted. In other words, in the present aspect, the reference arm 1040 is the optical path between the beam splitter 1020 and the reference mirror 1030 while the measurement arm 1050 is the optical path from the beam splitter 1020 to the subject's eye E; however, the other way around may also be employed.

The reference mirror 1030 is moved along the reference arm 1040 by the reference mirror driving mechanism 1035. Thereby, the optical path length of the reference arm 1040 is changed.

The measurement arm 1050 guides the measurement light generated by the beam splitter 1020 to the subject's eye E, and also guides the return light of the measurement light from the subject's eye E to the beam combiner 1020. The typical measurement arm 1050 includes an optical scanner (not shown in the drawings) such as a galvano mirror scanner and realizes various kinds of scan modes (e.g., B-scan, three dimensional scan, etc.).

On the other hand, the reference light generated by the beam splitter 1020 is guided to the reference mirror 1030 by the reference arm 1040, reflected by the reference mirror 1030, and returned to the beam combiner 1020.

The beam combiner 1020 superposes the return light of the measurement light from the subject's eye E and the reference light reflected by the reference mirror 1030. Such a superposition generates interference light that includes information on the subject's eye E. The generated interference light is guided to the photodetector 1060. The photodetector 1060 detects the interference light and outputs an electric signal (an interference signal).

The OCT data generating unit 1070 generates OCT data based on the interference signal. Typically, the OCT data generating unit 1070 constructs an OCT image according to the scan mode applied to the subject's eye E (e.g., B-scan image, three dimensional image, etc.). The process of generating an intensity profile from an interference signal and the process of performing imaging process on the intensity profile are both known.

The processing unit 1080 controls the reference mirror driving mechanism 1035 to place the partial data of the OCT data corresponding to the predetermined part of the eye at the standard depth level that has been set based on the predetermined ocular parameter value. For example, the processing unit 1080 controls the reference mirror driving mechanism 1035 to place the image region (the RPE region) in the OCT image corresponding to the retinal pigment epithelium of the subject's eye E at the predetermined standard depth level.

To do so, the processing unit 1080 performs the following processes, for example: analyzing the OCT image to detect an image region (an ILM region) corresponding to the retinal surface; setting a high-brightness and clear region that is located at a level deeper than the ILM region by about 0.5 mm, as the RPE region; averaging the depth levels (z coordinates) of a plurality of points (a plurality of pixels) in the RPE region; calculating the deviation of the average depth level (average z coordinate of the RPE region) thus obtained, with respect to the standard depth level; and controlling the reference mirror driving mechanism 1035 to move the reference mirror 1030 in a direction and by a distance that compensate the calculated deviation. Alternatively, the processing unit 1080 may be configured to analyze the OCT image to detect the high-brightness region mentioned above, without ILM region detection, and set the detected region as the RPE region.

By repeating a series of such processes, Z-lock can be performed to maintain the state where the average depth level of the RPE region is located at the standard depth level. Further, setting the standard depth level as described above may yield an OCT image in which the edge of the image of the retinal surface is placed on the lateral side of the image frame. In other words, by setting the standard depth level as described above, the retinal image does not protrude from (go beyond) the upper edge of the image frame, and thus a fold-over artifact does not occur.

<About Setting of Standard Depth Level>

This section describes standard depth levels applicable to Auto-Z and Z-lock in the case where a B-scan with the line length of 12 mm, which is one of typical wide-angle OCT scan modes, is employed. In particular, this section describes conditions in which fold-over artifacts of an eye fundus do not occur in the case where a B-scan with the line length of 12 mm is applied to the fundus of an eye having a relatively long axial length such as a myopic eye.

First, an eye ball is modeled in the following manner. It is assumed that the shape of the posterior pole of the fundus is defined by, for example, the retinal pigment epithelium (RPE). It is also assumed that the shape of the posterior pole may be approximated by an ellipse (ellipsoid).

Referring to the linear regressions described in David A. Atchison et al., "Shape of the Retinal Surface in Emmetropia and Myopia", Investigative Ophthalmology & Visual Science, August 2005, Vol. 46, No. 8, PP. 2698-2707, the curvature radius of retina (the radius of the major axis of the ellipse that approximates the shape of the retina, or the semi-major axis length) "Rz", and the equatorial radii "Rx" and "Ry" are respectively represented as follows. Here, the unit of length is millimeter. "D" denotes the unit "diopter" of the optical powers of eyes.

$$Rz(mm) = 0.163\,D + 10.148$$

$$Rx(mm) = -0.043\,D + 11.455$$

$$Ry(mm) = -0.090\,D + 11.365$$

From them, the following assumptions are made: the axial length corresponding to the optical power 0 D is 24 mm; the optical power changes by −3 D for each 1 mm extension of the axial length; and the retinal thickness of the thick part is 500 um.

The following methods and techniques are used for setting a standard depth level so that a fold-over artifact of the fundus does not occur in the case where a B-scan with the line length of 12 mm is applied to eye fundus.

1. The retinal shape simulation is performed based on the eye model. As described above, it is assumed that the cross sectional image of the retina has an elliptic shape, the retinal curvature radius corresponds to the length of the semi-major axis, and the equator corresponds to the minor axis.

2. An image acquired by applying an OCT scan (a B-scan with the line length of 12 mm) to the fundus is obtained by simulation.

Figure 2:
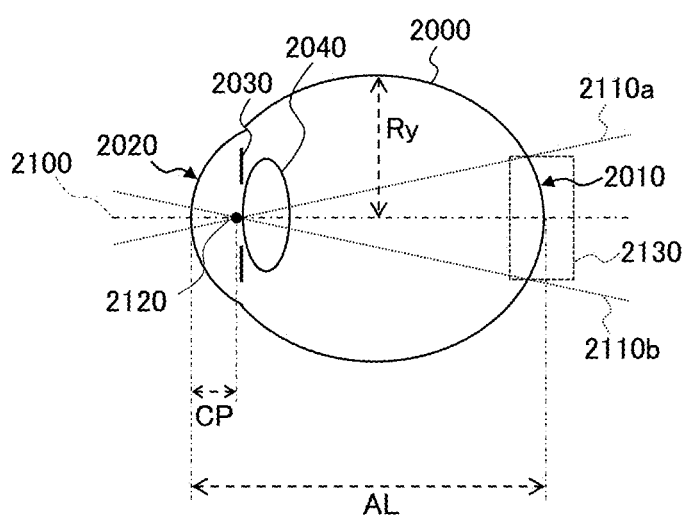
FIG. 2 is a schematic diagram for describing the ophthalmic apparatus according to an aspect example.

FIG. 2 shows an eye model used in a simulation example. As to the eye model 2000, the reference character 2010 denotes an eye fundus of an elliptic shape (posterior pole, retina, retinal pigment epithelium), the reference character 2020 denotes a cornea, the reference character 2030 denotes an iris, and the reference character 2040 denotes a crystalline lens.

Further, the reference character 2100 denotes the central axis (the scan central axis) of the OCT scan (the B-scan with the line length of 12 mm). The scan central axis 2100 is assumed to coincide with the axis of the eye model 2000. The axis of the eye model 2000 is typically, a straight line connecting the apex of the cornea 2020 and the center of the fundus 2010. The reference characters 2110*a* and 2110*b* denote the paths of the measurement light at maximum deflection angles in the B-scan having the line length of 12 mm centered on the scan central axis 2100. The reference character 2120 denotes the center point (a fixed point, a pivot point) of the measurement light being deflected (swung) in the B-scan having the line length of 12 mm. The reference character 2130 denotes an area (an imaging area) measured and imaged through the B-scan having the line length of 12 mm.

Further, as described above, the equatorial radius in the y direction is denoted by "Ry", the axial length of the eye model 2000 is denoted by "AL", and the distance from the corneal apex to the pivot point is denoted by "CP". Referring to Arthur G. Bennett et al., "Improvements on Littmann's method of determining the size of retinal features by fundus photography", Graefe's Arch Olin Exp Ophthalmol (1994), 232: 361-367, the standard value 1.82 mm will be adopted as the distance from the corneal apex to the pivot point "CP". Given that the focal length (f) of a standard eye is 17 mm, the maximum deflection angle (θ) of the measurement light when applying the B-scan having the line length of 12 mm to such an eye becomes 19.44 degrees. In other words, the angle formed by the scan central axis 2100 and the path 2110*a* (or the path 2110*b*) in that case becomes 19.44 degrees. This corresponds to the case where the B-scan having the line length of 12 mm is applied to an eye model having the optical power 0 D.

Further, simulations of the states of Z-lock are carried out for several values of the standard depth level. In what follows, the number of pixels from the upper edge to the lower edge of the image frame (the number of pixels in the z direction) is 992, and simulations are performed for the following cases: the case where the standard depth level is set at the level corresponding to the 450th pixel from the upper edge of the image frame; and the case where the standard depth level is set at the level corresponding to the 550th pixel from the upper edge of the image frame.

Note that it is generally known that the closer the standard depth level is to the lower edge of the image frame, the lower the image quality of the fundus depicted becomes. On the other hand, the closer the standard depth level is to the upper edge of the image frame, the higher the possibility that a fold-over artifact of the fundus will occur. The present example is directed to optimize the standard depth levels that are subjected to such restrictions or a dilemma.

Here, as described above, it is assumed that the Auto-Z and Z-lock are executed with reference to the average depth level of the image region corresponding to the retinal pigment epithelium (the RPE region).

Furthermore, simulations of the states of Z-lock are carried out for several values of the optical power. In the following, the optical powers −6 D and −10 D will be considered. In addition, comparisons and discussions will be made in a pivot point range of 1.17 to 2.47 mm, in consideration of the individual differences in the position of pivot point (CP=1.27 to 2.37 mm) described in Arthur G. Bennett et al. and also in consideration of the allowable range of the working distance (error) of the ophthalmic apparatus (e.g., ±0.1 mm).

Figure 3:
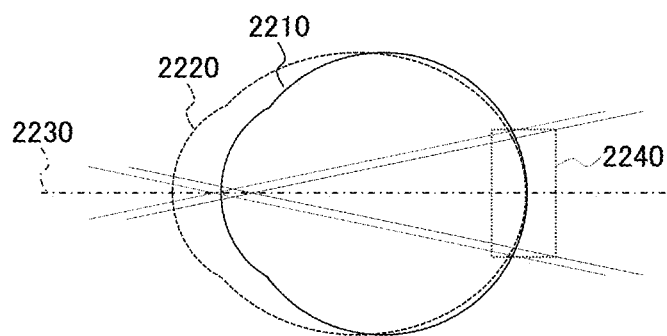
FIG. 3 is a schematic diagram for describing the ophthalmic apparatus according to an aspect example.

To begin with, simulations of a plurality of retinal shapes respectively corresponding to a plurality of different axial lengths are carried out in order to understand the differences in the retinal shape due to the differences in the axial length. FIG. 3 shows an example of such simulations. The eye model 2210 is an eye model having an axial length corresponding to the optical power 0 D, and the eye model 2220 is an eye model having an axial length corresponding to the optical power −6 D. The reference character 2230 denotes a scan central axis. Comparing the shapes of the eye models 2210 and 2220 in the region 2240, no significant difference is seen.

Thus, as long as the difference in the retinal shape according to the difference in the axial length (the optical power) is taken into consideration, its impact on OCT images is thought to be not so significant, and the occurrence and degree of fold-over artifacts of eye fundus are not also thought to be not so significant. Therefore, various kinds of parameters that may affect OCT images will be examined. Below, three parameters, namely the standard depth level, the optical power, and the position of the pivot point, will be examined. It should be noted that the same or similar examinations may be performed for any parameters other than the three, and the results of such examinations may be taken into consideration.

First, the influence of the standard depth level on OCT images will be described with reference to FIG. 4A and FIG. 4B. As described above, the number of pixels in the depth direction (z direction) is 992, and the depth "z" is represented by pixel numbers (0 to 991). Here, the number of the pixel closest to the cornea is "0", and the pixel number (integer) increases as the distance from the cornea increases. The direction in which the pixel number increases is defined as "+z direction".

Figure 4A:
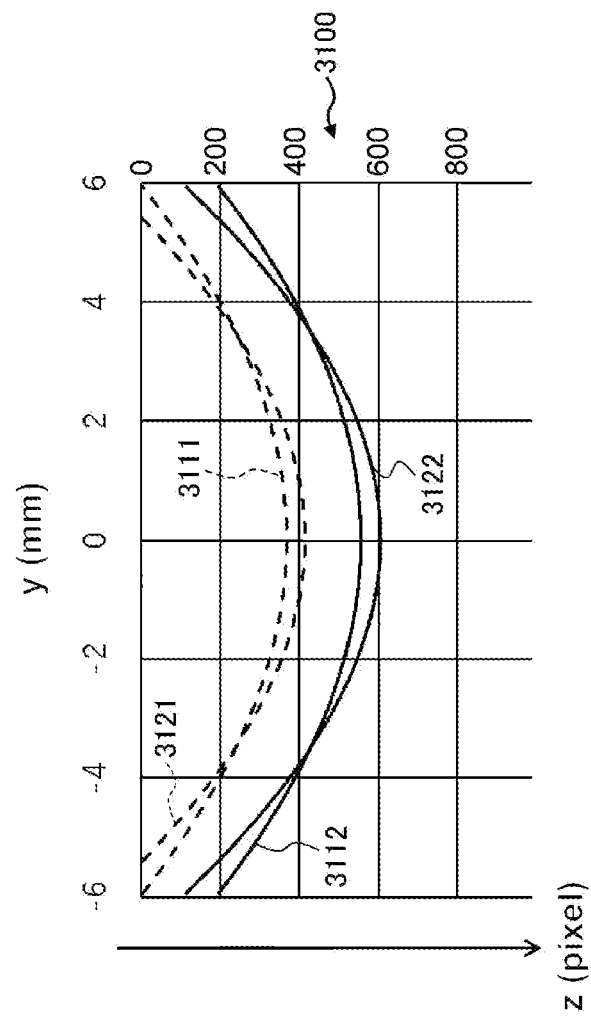
FIG. 4A is a schematic diagram for describing the ophthalmic apparatus according to an aspect example.
Figure 4B:
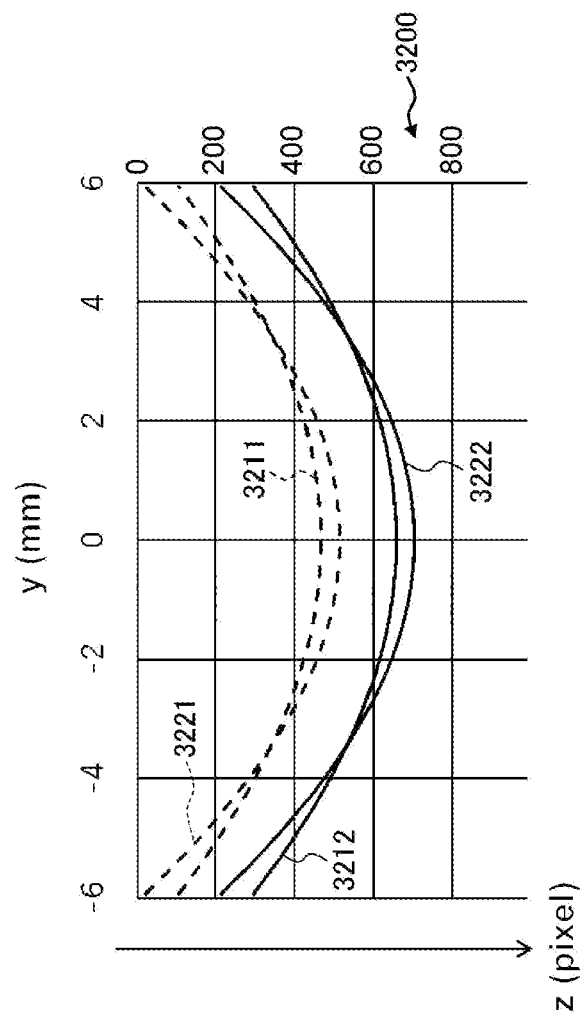
FIG. 4B is a schematic diagram for describing the ophthalmic apparatus according to an aspect example.

FIG. 4A shows the results of the shape and the position of the retina obtained by performing the simulation with the standard depth level set to "z=450", and FIG. 4B shows the results of the shape and the position of the retina obtained by performing the simulation with the standard depth level set to "z=550".

The simulations employ the following conditions: the equatorial diameter is set to 23.25 mm; the axial length corresponding to the optical power 0 D is set to 24 mm; the axial length corresponding to the optical power −6 D is set to 26 mm; the OCT scan mode is set to be a B-scan along the vertical direction (y direction) with the line length of 12 mm in the case where the optical power is 0 D (the focal length f=17 mm); and the position of the pivot point (pivot position) of the measurement light for the B-scan is set at the position apart from the corneal apex by 1.82 mm in the +z direction. The unit of the coordinates in the y direction is the distance "mm", and the y coordinates are defined in the range of "−6 mm to +6 mm" having "0" as the scan central axis described above. The y coordinates are defined in the case where the optical power is 0 D (the focal length f=17 mm).

In the simulation result 3100 (FIG. 4A) corresponding to the standard depth level "z=450", the reference character 3111 denotes the position and the shape of the retinal surface corresponding to the optical power 0 D (the axial length of 24 mm), the reference character 3112 denotes the position and the shape of the retinal pigment epithelium corresponding to the same optical power 0 D (the axial length of 24 mm). Here, as described above, the location of the retinal pigment epithelium is set at a position where the retinal surface is shifted by 0.5 mm in the +z direction (the same applies below).

In addition, the reference character 3121 denotes the position and the shape of the retinal surface corresponding to the optical power −6 D (the axial length of 26 mm), and the reference character 3122 denotes the position and the shape of the retinal pigment epithelium corresponding to the same optical power −6 D (the axial length of 26 mm).

As can be seen from the simulation result 3100, the entire retinal surface 3111 (y=−6 to +6) is depicted in the image frame (the imaging area) in the case of the optical power 0 D (the axial length of 24 mm). On the other hand, both edges of the retinal surface 3121 (one edge near y=−6 and the other edge near y=+6) are not depicted in the image frame in the case of the optical power −6 D (the axial length 26 mm). Such a simulation result 3100 indicates that there is a possibility that both edges of the retinal surface may protrude from the image frame and a fold-over artifact may occur when the above conditions are applied to photography of a myopic eye with the optical power of about −6 D (the axial length of 26 mm or an eye with higher myopia (an eye with longer axial length).

Moving now on to FIG. 4B. In the simulation result 3200 corresponding to the standard depth level "z=550", the reference character 3211 denotes the position and the shape of the retinal surface corresponding to the optical power 0 D (the axial length of 24 mm), and the reference character 3212 denotes the position and the shape of the retinal pigment epithelium corresponding to the same optical power 0 D (the axial length of 24 mm).

Furthermore, the reference character 3221 denotes the position and the shape of the retinal surface corresponding to the optical power −6 D (the axial length of 26 mm), and the reference character 3222 denotes the position and the shape of the retinal pigment epithelium corresponding to the same optical power −6 D (the axial length of 26 mm).

As can be seen from the simulation result 3200, the entire retinal surface (y=−6 to +6) is depicted in the image frame not only in the case of the optical power 0 D (the axial length of 24 mm), but also in the case of the optical power −6 D (the axial length of 26 mm). Further, in the case of the optical power −6 D (the axial length of 26 mm), both edges of the retinal surface 3221 are located barely within the image frame. Such a simulation result 3200 shows that there is a high possibility that the entire retinal surface will be depicted in the image frame and a fold-over artifact will not occur when the above conditions are applied to photography of a myopic eye with the optical power of about −6 D (the axial length of 26 mm) or an eye with lower myopia (an eye with shorter axial length).

As described thus far, examining and analyzing the simulation results 3100 and 3200 shown in FIG. 4A and FIG. 4B indicate that there is a possibility that the retinal surface may protrude from the image frame (the imaging area) and a fold-over artifact may occur already for a myopic eye with the optical power of about −6 D (the axial length of 26 mm) even with the standard depth level "z=450". In addition, examining and analyzing the simulation results 3100 and 3200 indicate that the shallower the standard depth level becomes (that is, the closer the standard depth level is to the upper edge of the image frame, or the smaller the z value becomes), the higher the risk becomes that the retinal surface may protrude from the imaging area and a fold-over artifact may occur, in the case where both the pivot position and the optical power are fixed.

Figure 5A:
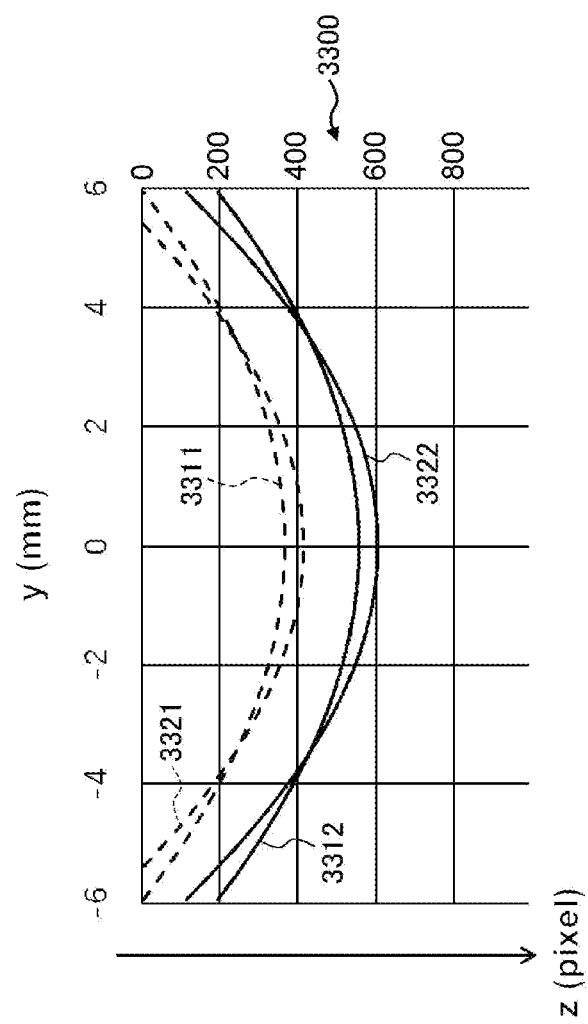
FIG. 5A is a schematic diagram for describing the ophthalmic apparatus according to an aspect example.
Figure 5B:
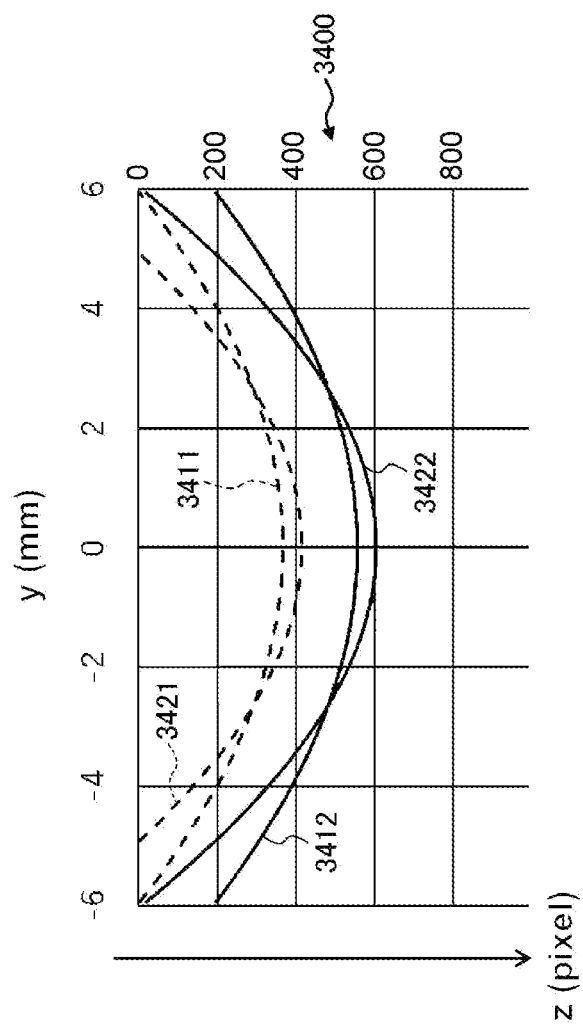
FIG. 5B is a schematic diagram for describing the ophthalmic apparatus according to an aspect example.

Next, the influence of the optical power on OCT images will be described with reference to FIG. 5A and FIG. 5B. Both FIG. 5A and FIG. 5B show the results of the shape and the position of the retina obtained by performing the simulation with the standard depth level set to "z=450".

The simulations employ the following conditions: the equatorial diameter is set to 23.25 mm; the axial length corresponding to the optical power 0 D is set to 24 mm; the axial length corresponding to the optical power −6 D is set to 26 mm; the axial length corresponding to the optical power −10 D is set to 27.33 mm; the OCT scan mode is set to be a B-scan along the vertical direction (y direction) with the line length of 12 mm in the case where the optical power is 0 D (the focal length f=17 mm); and the position of the pivot point (pivot position) of the measurement light for the B-scan is set at the position apart from the corneal apex by 1.82 mm in the +z direction. The unit of the coordinates in the y direction is the distance "mm", and the y coordinates are defined in the range of "−6 mm to +6 mm" having "0" as the scan central axis described above. The y coordinates are defined in the case where the optical power is 0 D (the focal length f=17 mm).

In the simulation result 3300 (FIG. 5A) corresponds to the optical power −6D, the reference character 3311 denotes the position and the shape of the retinal surface corresponding to the optical power 0 D (the axial length of 24 mm), and the reference character 3312 denotes the position and the shape of the retinal pigment epithelium corresponding to the same optical power 0 D (the axial length of 24 mm). These are presented to be compared with the followings. Namely, the reference character 3321 denotes the position and the shape of the retinal surface corresponding to the optical power −6 D (the axial length of 26 mm), and the reference character 3322 denotes the position and the shape of the retinal pigment epithelium corresponding to the same optical power −6 D (the axial length of 26 mm).

As can be seen from the simulation result 3300, the entire retinal surface 3311 (y=−6 to +6) is depicted in the image frame (the imaging area) in the case of the optical power 0 D (the axial length of 24 mm). On the other hand, both edges of the retinal surface 3321 (one edge near y=−6 and the other edge near y=+6) are not depicted in the image frame in the case of the optical power −6 D (the axial length 26 mm).

Moving now on to FIG. 5B. In the simulation result 3400 corresponding to the optical power −10D, the reference character 3411 denotes the position and the shape of the retinal surface corresponding to the optical power 0 D (the axial length of 24 mm), and the reference character 3412 denotes the position and the shape of the retinal pigment epithelium corresponding to the same optical power 0 D (the axial length of 24 mm). These are presented to be compared with the followings. Namely, the reference character 3421 denotes the position and the shape of the retinal surface corresponding to the optical power −10 D (the axial length of 27.33 mm), and the reference character 3422 denotes the position and the shape of the retinal pigment epithelium corresponding to the same optical power −10 D (the axial length of 27.33 mm).

As can be seen from the simulation result 3400, relatively wide areas of both edges of the retinal surface 3421 are not depicted in the image frame, and even both edges of the retinal pigment epithelium 3422 are placed barely within the image frame in the case of the optical power −10 D (the axial length of 27.33 mm).

As described thus far, examining and analyzing the simulation results 3300 and 3400 shown in FIG. 5A and FIG. 5B indicate that there is a high possibility that the retinal surface may significantly protrude from the image frame (the imaging area) and a fold-over artifact may occur for a high myopic eye with the optical power of about −10 D (the axial length of 27.33 mm) in the case of the standard depth level "z=450". In addition, indicated is the fact that the higher the optical power of a myopic eye becomes (that is, the greater the absolute value of the optical power that is a negative value becomes, or the higher the degree of myopia becomes), the higher the risk becomes that the retinal surface may protrude from the imaging area and a fold-over artifact may occur in the case where both the pivot position and the standard depth level are fixed.

Figure 6A:
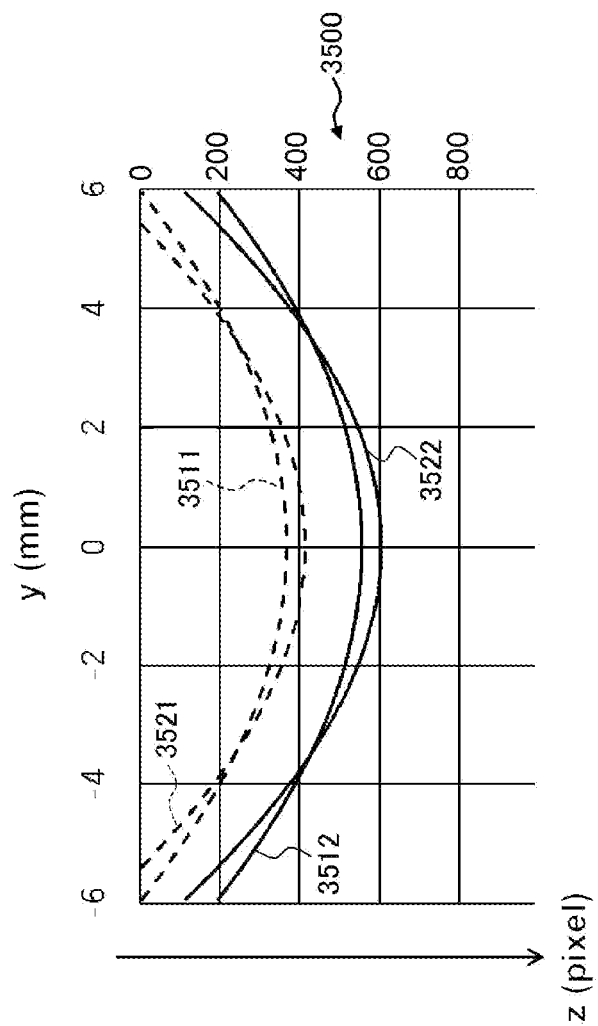
FIG. 6A is a schematic diagram for describing the ophthalmic apparatus according to an aspect example.
Figure 6B:
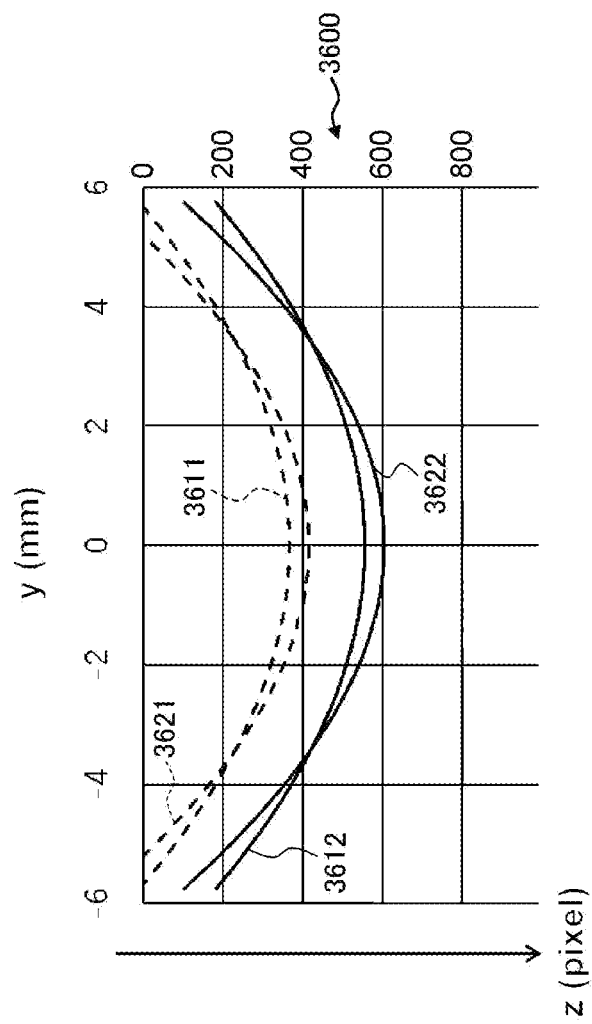
FIG. 6B is a schematic diagram for describing the ophthalmic apparatus according to an aspect example.
Figure 6C:
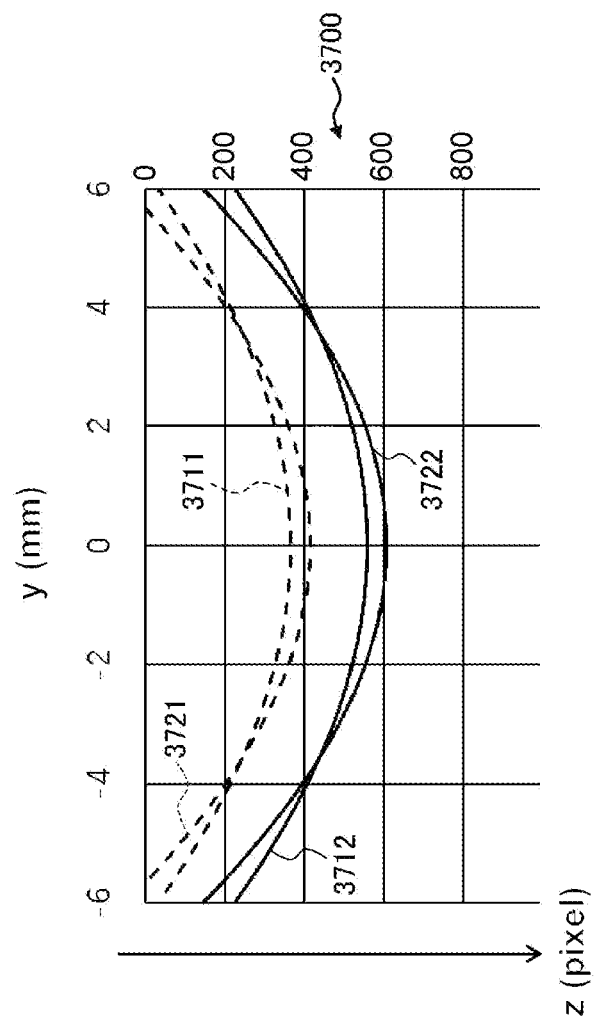
FIG. 6C is a schematic diagram for describing the ophthalmic apparatus according to an aspect example.

Finally, the influence of the pivot position on OCT images will be described with reference to FIG. 6A, FIG. 6B and FIG. 6C. FIG. 6A to FIG. 6C all show the results of the shape and the position of the retina obtained by performing the simulations with the standard depth level set to "z=450".

The simulations employ the following conditions: the equatorial diameter is set to 23.25 mm; the axial length corresponding to the optical power 0 D is set to 24 mm; the axial length corresponding to the optical power −6 D is set to 26 mm; and the OCT scan mode is set to be a B-scan along the vertical direction (y direction) with the line length of 12 mm in the case where the optical power is 0 D (the focal length f=17 mm). The unit of the coordinates in the y direction is the distance "mm", and the y coordinates are defined in the range of "−6 mm to +6 mm" having "0" as the scan central axis described above. The y coordinates are defined in the case where the optical power is 0 D (the focal length f=17 mm).

In the simulation result 3500 (FIG. 6A) corresponding to the standard pivot position "1.82 mm", the reference character 3511 denotes the position and the shape of the retinal surface corresponding to the optical power 0 D (the axial length of 24 mm), and the reference character 3512 denotes the position and the shape of the retinal pigment epithelium corresponding to the same optical power 0 D (the axial length of 24 mm). Further, the reference character 3521 denotes the position and the shape of the retinal surface corresponding to the optical power −6 D (the axial length of 26 mm), and the reference character 3522 denotes the position and the shape of the retinal pigment epithelium corresponding to the same optical power −6 D (the axial length of 26 mm).

As can be seen from the simulation result 3500, the entire retinal surface 3511 (y=−6 to +6) is barely depicted in the image frame (the imaging area) in the case of the optical power 0 D (the axial length of 24 mm). On the other hand, both edges of the retinal surface 3521 (one edge near y=−6 and the other edge near y=+6) are not depicted in the case of the optical power −6 D (the axial length 26 mm).

Moving now on to FIG. 6B. In the simulation result 3600 corresponding to the pivot position "1.17 mm", the reference character 3611 denotes the position and the shape of the retinal surface corresponding to the optical power 0 D (the axial length of 24 mm), and the reference character 3612 denotes the position and the shape of the retinal pigment epithelium corresponding to the same optical power 0 D (the axial length of 24 mm). In addition, the reference character 3621 denotes the position and the shape of the retinal surface corresponding to the optical power −6 D (the axial length of 26 mm), and the reference character 3622 denotes the position and the shape of the retinal pigment epithelium corresponding to the same optical power −6 D (the axial length of 26 mm).

As can be seen from the simulation result 3600, both edges of the retinal surface are not depicted in the image frame in both cases of the optical power 0 D (the axial length of 24 mm) and the optical power −6 D (the axial length of 26 mm). In particular, relatively wide areas of both edges of the retinal surface are not depicted in the case of the optical power−6 D (the axial length of 26 mm).

Next, moving on to FIG. 6C. In the simulation result 3700 corresponding to the pivot position "2.47 mm", the reference character 3711 denotes the position and the shape of the retinal surface corresponding to the optical power 0 D (the axial length of 24 mm), and the reference character 3712 denotes the position and the shape of the retinal pigment epithelium corresponding to the same optical power 0 (the axial length of 24 mm). In addition, the reference character 3721 denotes the position and the shape of the retinal surface corresponding to the optical power−6 D (the axial length of 26 mm), and the reference character 3722 denotes the position and the shape of the retinal pigment epithelium corresponding to the same optical power −6 D (the axial length of 26 mm).

As can be seen from the simulation result 3700, the entire retinal surface 3711 (y=−6 to +6) is depicted in the image frame (the imaging area) in the case of the optical power 0 D (the axial length of 24 mm). On the other hand, both edges of the retinal surface 3721 (one edge near y=−6 and the other edge near y=+6) are not depicted in the case of the optical power −6 D (the axial length 26 mm).

As described thus far, examining and analyzing the simulation results 3500 to 3700 shown in FIG. 6A to FIG. 6B indicate that there is a high possibility that a fold-over artifact may occur in the case where the pivot point is set at a position close to the cornea, that is, in the case where the value of the pivot position becomes smaller. In addition, indicated is the fact that the closer the pivot position is to the corneal apex, the higher the risk becomes that the retinal surface may protrude from the imaging area and a fold-over artifact may occur, in the case where both the optical power and the standard depth level are fixed.

According to the results of the above simulations as well as the examination and analysis thereof, the standard depth level for the present aspect may be set as in the following manner. The description of the present example related to the setting of the standard depth level will be provided with reference to FIG. 7A, FIG. 7B, and FIG. 7C.

Figure 7A:
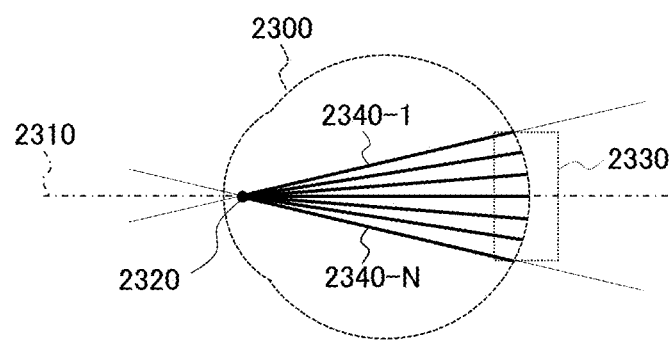
FIG. 7A is a schematic diagram or describing the ophthalmic apparatus according to an aspect example.
Figure 7B:
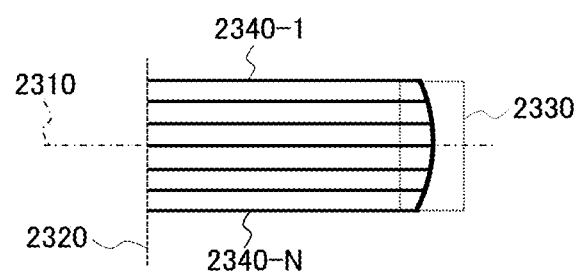
FIG. 7B is a schematic diagram for describing the ophthalmic apparatus according to an aspect example.
Figure 7C:
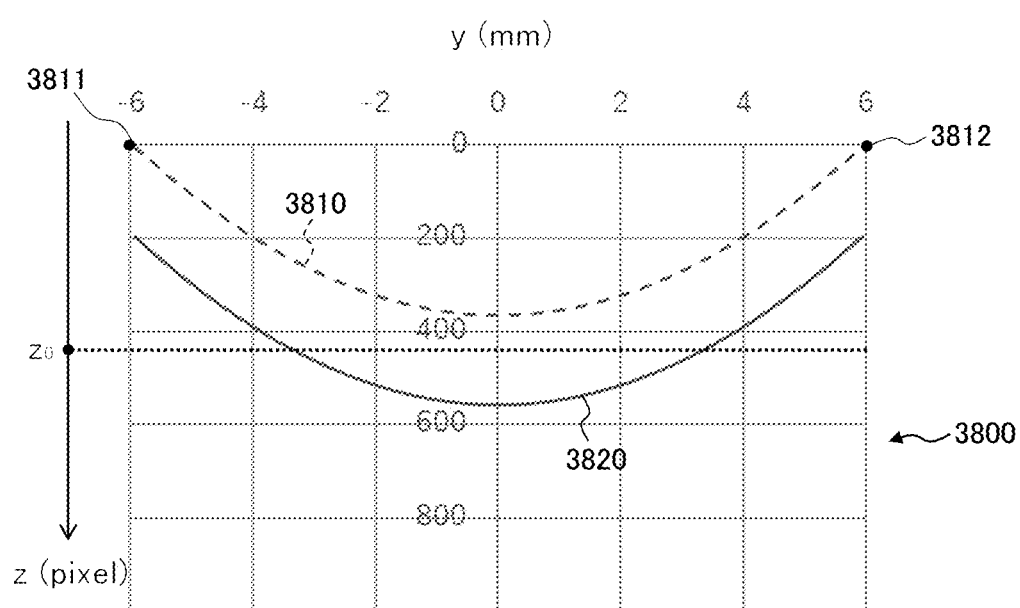
FIG. 7C is a schematic diagram for describing the ophthalmic apparatus according to an aspect example.

As shown in FIG. 7A, it is assumed that an OCT scan is applied to the fundus of the subject's eye (or the eye model) 2300. The OCT scan of the present example is a B-scan, and is executed by deflecting and swinging the measurement light around the pivot point 2320 located on the axis 2310 of the subject's eye 2300. Such an OCT scan yields the number "N" of A-scan images 2340-$n$ (n=1, 2, . . . , N) corresponding to the number "N" of A-lines arranged to pass through the imaging area 2330. The number "N" of A-scan images 2340-1 to 2340-N are arranged in a fan shape centered on the pivot point 2320.

A B-scan image is constructed based on the number "N" of A-scan images 2340-1 to 2340-N thus acquired. Typically, a B-scan image is constructed by converting the array or arrangement of the number "N" of A-scan images 2340-1 to 2340-N from the fan-shaped arrangement shown in FIG. 7A to the parallel arrangement shown in FIG. 7B. A standard depth level may be set using the B-scan image constructed in this way. Examples of some conditions for setting the standard depth level will be described based on the simulation result 3800 shown in FIG. 7C.

The first exemplary condition is that the retinal surface (the ILM region) 3810 intersects the lateral side of the image frame. That is, the first exemplary condition is that the left edge (y=−6) of the retinal surface 3810 is located on the left lateral side, and the right edge (y=+6) is located on the right lateral side. In other words, the first exemplary condition is that the origin in the z direction (z=0) is set to be located on the upper edge of the image frame, and the +z direction is the direction from the upper edge to the lower edge of the image frame, as well as that "R(y=−6)≥0" and "R(y=+6)≥0" are both satisfied where the curve representing the retinal surface 3810 is represented by "z=R(y)".

The second exemplary condition is the assumption that the retinal pigment epithelium (RPE region) is located at the position (level) 3820 shifted from the retinal surface 3810 by a predetermined distance in the +z direction. The predetermined distance may be set to 0.5 mm, as described above, for example, but is not limited to this.

The third exemplary condition is that the average depth level of the retinal pigment epithelium 3820 in the imaging area 2330 (−6≤y≤+6), or a position whose z coordinate value is larger than the average depth level (that is, the average depth level, or, a level or position located on the bottom edge of the image frame with respect to the average depth level) is set as the standard depth level.

According to the various kinds of simulations mentioned above, the following knowledge may be obtained. First, the retinal image does not go beyond the upper edge of the image frame and a fold-over artifact does not occur, as long as there is no inclination (slant, slope, tilt), until the axial length reaches the length corresponding to the optical power−6 D in the case where the standard depth level is set to "z=450". On the other hand, imaging may be performed with a certain margin in the case where the standard depth level is set to "z=550".

Further, there is a possibility that a fold-over artifact of the retina may occur even if the standard depth level is set to "z=450" in the case where the axial length is the length corresponding to the optical power −10 D.

In addition, considering the fact that the position of the pivot point varies depending on individual differences and alignment errors, there is a possibility that a fold-over artifact occurs even if the axial length is about the length corresponding to the optical power −6 D in the case where the pivot point is shifted to the corneal side.

<Embodiment Examples>

Some examples of an ophthalmic apparatus for realizing the above-described aspect example will be described. The ophthalmic apparatus according to the present embodiment example has a configuration for applying an OCT scan to an eye fundus. The following aspect example describes an example in which a swept source OCT apparatus and a fundus camera are combined, but embodiment examples are not limited to such a configuration. For example, a spectral domain OCT apparatus including a low coherence light source and a spectrometer may be employed instead of the swept source OCT apparatus.

Figure 8:
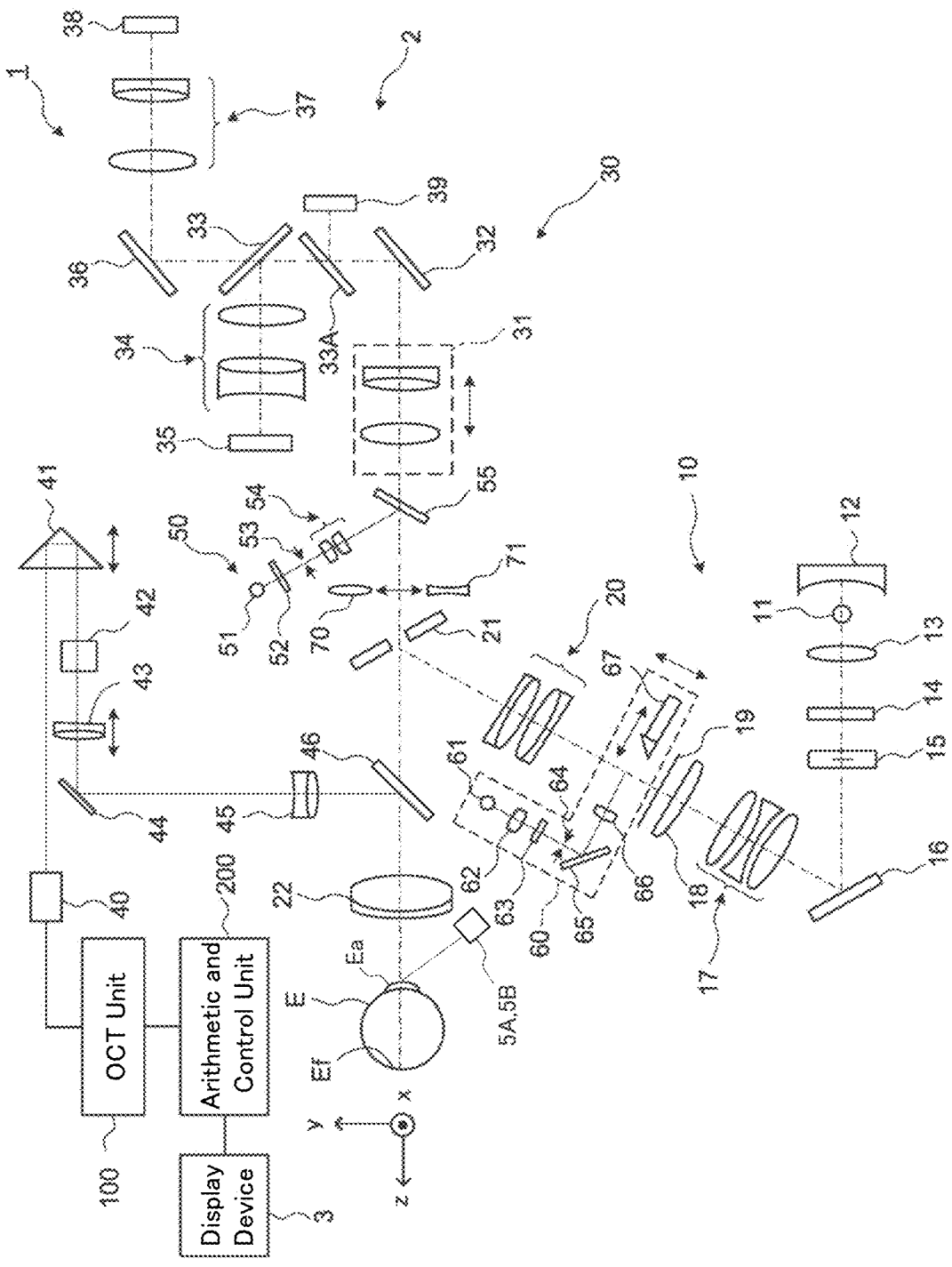
FIG. 8 is a schematic diagram showing an example of the configuration of the ophthalmic apparatus according to an embodiment example.

The ophthalmic apparatus 1 of the present embodiment example shown in FIG. 8 includes the fundus camera unit 2, the OCT unit 100, and the arithmetic and control unit 200. The fundus camera unit 2 is provided with an optical system and a mechanism for acquiring front images of the subject's eye E (e.g., the anterior segment Ea, the fundus Ef). The OCT unit 100 includes an optical system and a mechanism for performing OCT scans. The arithmetic and control unit 200 includes a processor configured and programmed to execute various kinds of calculations and controls. In addition to these, the ophthalmic apparatus 1 includes a member for supporting the face of the subject (e.g., a chin rest, a forehead rest) and a lens unit for switching the sites subjected to OCT scans (e.g., an attachment for an anterior segment OCT). Further, the ophthalmic apparatus 1 includes a pair of the anterior segment cameras 5A and 5B.

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes an objective function, for example, by reading out and executing a program stored in a storage circuit or a storage device.

The fundus camera unit 2 is provided with an optical system for photographing the anterior segment Ea and the fundus Ef. Images obtained by the fundus camera unit 2 include front images such as observation images and photographed images. An observation image is obtained by capturing a moving image using near-infrared light. A photographed image is a still image obtained by using flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2, and the return light thereof is directed to the OCT unit 100 through the same optical path.

The observation light source 11 of the illumination optical system 10 outputs continuous light (observation illumination light) containing a near-infrared component. The observation illumination light is reflected by the reflection mirror 12 having a curved reflection surface, passes through the condenser lens 13, and becomes near-infrared light after passing through the visible cut filter 14. Further, the observation illumination light is once converged at a location near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the anterior segment Ea or the fundus Ef). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light passes through the half mirror 33A, is reflected by the dichroic mirror 33, and forms an image on the light receiving surface of the image sensor 35 by the condenser lens 34. The image sensor 35 detects the return light at a predetermined frame rate. Note that the focus of the photographing optical system 30 is adjusted with respect to the fundus Ef or the anterior segment Ea.

The photographing light source 15 outputs flash light (photographing illumination light) containing a visible component (and near-infrared component, optionally). The photographing illumination light passes through the same route as that of the observation illumination light and is projected onto the fundus Ef. The return light of the photographing illumination light from the subject's eye E is guided along the same route as that of the return light of the observation illumination light to the dichroic mirror 33, passes through the dichroic mirror 33, is reflected by the mirror 36, and forms an image on the light receiving surface of the image sensor 38 by the condenser lens 37.

The liquid crystal display (LCD) 39 displays a fixation target and a visual acuity measurement target. Part of the light beam output from the LCD 39 (fixation light beam, visual target light beam) is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

The change in the fixation position is carried out by changing the display position of a bright spot or the like on the LCD 39. The display position of the bright spot or the like is controlled by the main controller 211 described later. The main controller 211 displays the bright spot or the like at a position on the screen of the LCD 39 corresponding to the fixation position set by a predetermined method or technique. The method or technique of setting the fixation position is carried out using, for example, the user interface 240 described later. Further, the ophthalmic apparatus 1 may be configure to display the bright spot or the like at a predetermined position according to an imaging mode. Examples of the imaging mode include the macular imaging mode, the optic nerve head imaging mode, the panoramic mode, and the like.

The alignment optical system 50 generates an alignment indicator used for the alignment of the optical system with respect to the subject's eye E. The alignment light output from the light emitting diode (LED) 51 travels through the diaphragms 52 and 53, and the relay lens 54, is reflected by the dichroic mirror 55, passes through the aperture part of the aperture mirror 21. The light that has passed through the aperture part of the aperture mirror 21 then penetrates the dichroic mirror 46, and is projected onto the subject's eye E by the objective lens 22. The return light of the alignment light (e.g., the cornea reflection light, the fundus reflection light) passes through the same route as that of the return light of the observation illumination light and is guided to the image sensor 35. Based on the received image, manual alignment and/or automatic alignment may be carried out. The received image is referred to as an alignment indicator image.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 may be inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light then is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef. The fundus reflection light of the focus light passes through the same route as that of the return light of the alignment light and is guided to the image sensor 35. Based on the received image, manual focusing and/or automatic focusing may be carried out. The received image is referred to as a split indicator image.

The diopter correction lenses 70 and 71 can be selectively inserted to a position on the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning. The dichroic mirror 46 reflects the light of wavelength bands used for OCT scanning while transmitting the light for fundus photography. Listed from the OCT unit 100 side, the collimator lens unit 40, the optical path length changing unit 41 (OPL changing unit 41), the optical scanner 42, the OCT focusing lens 43, the mirror 44, and the relay lens 45 are provided and arranged in the optical path for OCT scanning.

The optical path length changing unit 41 is movable in the directions indicated by the arrow in FIG. 8, and changes the optical path length for OCT scanning. The change in the optical path length for OCT scanning may be utilized for correcting the optical path length according to the axial length, and for adjusting the interference conditions and states. The optical path length changing unit 41 includes a corner cube and a mechanism for moving the corner cube.

The optical scanner 42 is arranged at a position substantially optically conjugate with the pupil of the subject's eye E. The optical scanner 42 deflects the measurement light LS that passes through the optical path for OCT scanning. The optical scanner 42 is, for example, a galvano mirror scanner for two dimensional scanning.

The OCT focusing lens 43 is moved along the optical path of the measurement light LS in order to perform the focus adjustment of the optical system for OCT scanning. The movement of the photography focusing lens 31, the movement of the focus optical system 60, and the movement of the OCT focusing lens 43 may be controlled in an interlocking manner.

The ophthalmic apparatus 1 may include a supplementary lens unit (not shown in the drawings) that may be arranged on the front side of the objective lens 22, that is, that may be arranged in a position between the subject's eye E and the objective lens 22. The supplementary lens unit includes, for example, a lens group having a positive refractive power. The supplementary lens unit is retracted from the optical path when applying an OCT scan to the fundus Ef, and is inserted into the optical path when applying an OCT scan to the anterior segment Ea. The movement (insertion into and removal from the optical path) of the supplementary lens unit is performed electrically or manually.

The anterior segment cameras 5A and 5B are used to determine the relative position between the optical system of the ophthalmic apparatus 1 and the subject's eye E, as described in the invention disclosed in Japanese Unexamined Patent Application Publication No. 2013-248376 (US Patent Application Publication No. 2015/0085252). The anterior segment cameras 5A and 5B are provided on the surface, facing the subject's eye E, of the housing (of the fundus camera unit 2 etc.) in which an optical system is stored. The ophthalmic apparatus 1 determines a three dimensional relative position between the optical system and the subjects eye E by analyzing two anterior segment images acquired substantially simultaneously from mutually different directions by the anterior segment cameras 5A and 5B. The analysis techniques of the two anterior segment images may be the same as those disclosed in Japanese Unexamined Patent Application Publication No. 2013-248376 (US Patent Application Publication No. 2015/0085252). Further, the number of anterior segment cameras may be any number of two or more.

The present example is configured to obtain the position of the subject's eye E (therefore, the relative position between the subject's eye E and the optical system) by using two or more anterior segment cameras; however, applicable methods and techniques for obtaining the position of the subject's eye E are not limited to this. The position of the subject's eye E can be determined, for example, by analyzing a front image of the subject's eye E such as an observation image of the anterior segment Ea. Another example may be provided with a means or device of projecting an indicator on the cornea of the subject's eye E, and may determine the position of the subject's eye E based on the position at which the indicator is projected (in other words, based on a state of a detected cornea reflection light beam of the indicator).

Figure 9:
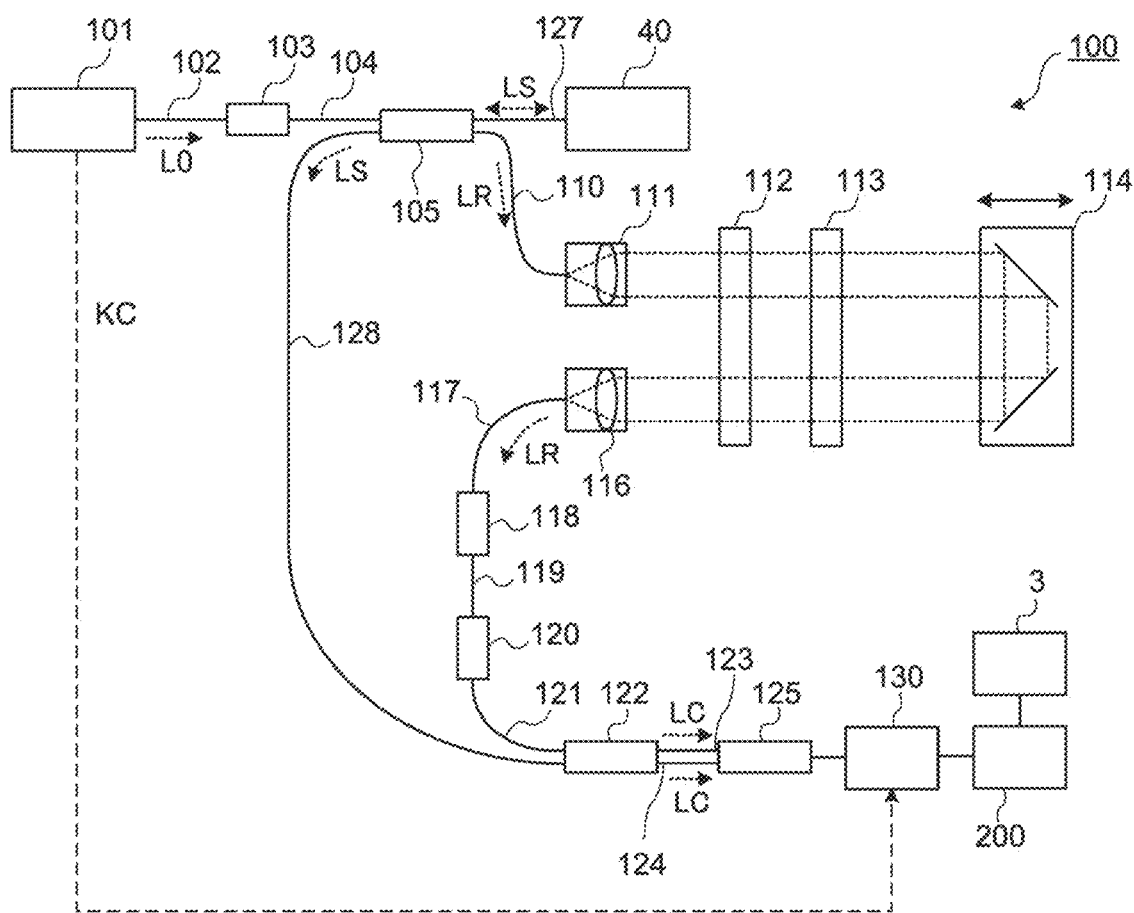
FIG. 9 is a schematic diagram showing an example of the configuration of the ophthalmic apparatus according to an embodiment example.

As illustrated in FIG. 9, the OCT unit 100 is provided with the optical system for performing swept source OCT. The optical system includes an interference optical system configured to split the light emitted from the light source of wavelength tunable type (or wavelength sweeping type) into measurement light and reference light, superpose the return light of the measurement light from the subject's eye E and the reference light having traveled through the reference optical path to generate interference light, and detect the interference light. The result of the detection (detection signal) obtained by the interference optical system is transmitted to the arithmetic and control unit 200.

The light source unit 101 includes, for example, a near-infrared tunable laser configured to vary the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR.

The reference light LR is guided through the optical fiber 110 to the collimator 111, is converted into a parallel light beam by the collimator 111, travels through the optical path length correction member 112 and the dispersion compensation member 113, and is guided to the corner cube 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other. The corner cube 114 is movable along the incident direction of the reference light LR. With this, the optical path length of the reference light LR is changed.

The reference light LR that has passed through the corner cube 114 travels through the dispersion compensation member 113 and the optical path length correction member 112, is converted from the parallel light beam to a convergent light beam by the collimator 116, and is incident on the optical fiber 117. The reference light LR incident on the optical fiber 117 is guided to the polarization controller 118, and the polarization state of the reference light LR is regulated by the polarization controller 118. Then, the reference light LR is guided to the attenuator 120 by the optical fiber 119, and the light amount of the reference light LR is regulated by the attenuator 120. Subsequently, the reference light LR is guided to the fiber coupler 122 by the optical fiber 121.

Meanwhile, the measurement light LS generated by the fiber coupler 105 is guided through the optical fiber 127 and is converted to a parallel light beam by the collimator lens unit 40. Then, the measurement light LS passes through the optical path length changing unit 41, the optical scanner 42, the OCT focusing lens 43, the mirror 44, and the relay lens 45, and then reaches the dichroic mirror 46. The measurement light LS is reflected by the dichroic mirror 46, is refracted by the objective lens 22, and is incident on the subject's eye E. In the case where an OCT scan is applied to the anterior segment Ea, the measurement light LS refracted by the objective lens 22 is further refracted by the lens group in the supplementary lens unit described above, and then projected onto the anterior segment Ea. The measurement light LS is reflected and scattered at various depth positions of the fundus Ef or the anterior segment Ea. The return light of the measurement light LS from the subject's eye E travels along the same route as the outward way in the opposite direction, is directed to the fiber coupler 105, and then reaches the fiber coupler 122 via the optical fiber 128.

The fiber coupler 122 couples (superposes) the measurement light LS incident through the optical fiber 128 and the reference light LR incident through the optical fiber 121, to generate interference light. The fiber coupler 122 splits the interference light at a predetermined splitting ratio (e.g., 1 to 1) to generate a pair of interference light LC. The pair of the interference light LC is guided to the detector 125 through a pair of the optical fibers 123 and 124, respectively.

The detector 125 is, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends such an output (detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 optically delays one of the two pieces of split light obtained by splitting the light L0 of each output wavelength. Then, the light source unit 101 generates the clock KC based on the result of the detection of the combined light generated from the resulting two pieces of split light. The DAQ 130 performs the sampling of the detection signal input from the detector 125 based on the clock KC. The DAQ 130 sends the sampling result of the detection signal from the detector 125, to the arithmetic and control unit 200.

The present example is provided with both the optical path length changing unit 41 configured for changing the length of the optical path of the measurement light LS (the measurement optical path, the measurement arm), and the corner cube 114 configured for changing the length of the optical path of the reference light LR (the reference optical path, the reference arm); however, some other examples may only include either one of the optical path length changing unit 41 and the corner cube 114. Further other examples may employ an optical member other than the optical path length changing unit 41 and the corner cube 114 in order to change the difference between the measurement optical path length and the reference optical path length.

The polarization controllers 103 and 118 may have known configurations. For example, the polarization controller 103 (118) includes one or more winding parts around which part of an optical fiber is wound, and a rotation mechanism for rotating each winding part. Alternatively, the polarization controller 103 (118) may include the following elements: a collimator lens for collimating light emitted from an optical fiber into a parallel light beam; a first quarter-wave plate ($\lambda/4$ plate), a half-wave plate ($\lambda/2$ plate), and a second quarter-wave plate, which are sequentially arranged in the optical path of the parallel light beam; a collimator lens for converging the parallel light beam that has passed through the three wave plates onto the end of an optical fiber; and a rotation mechanism for rotating each of the first quarter-wave plate, the half-wave plate, and the second quarter-wave plate. Each of the polarization controllers 103 and 118 is controlled by the main controller 211.

Figure 10:
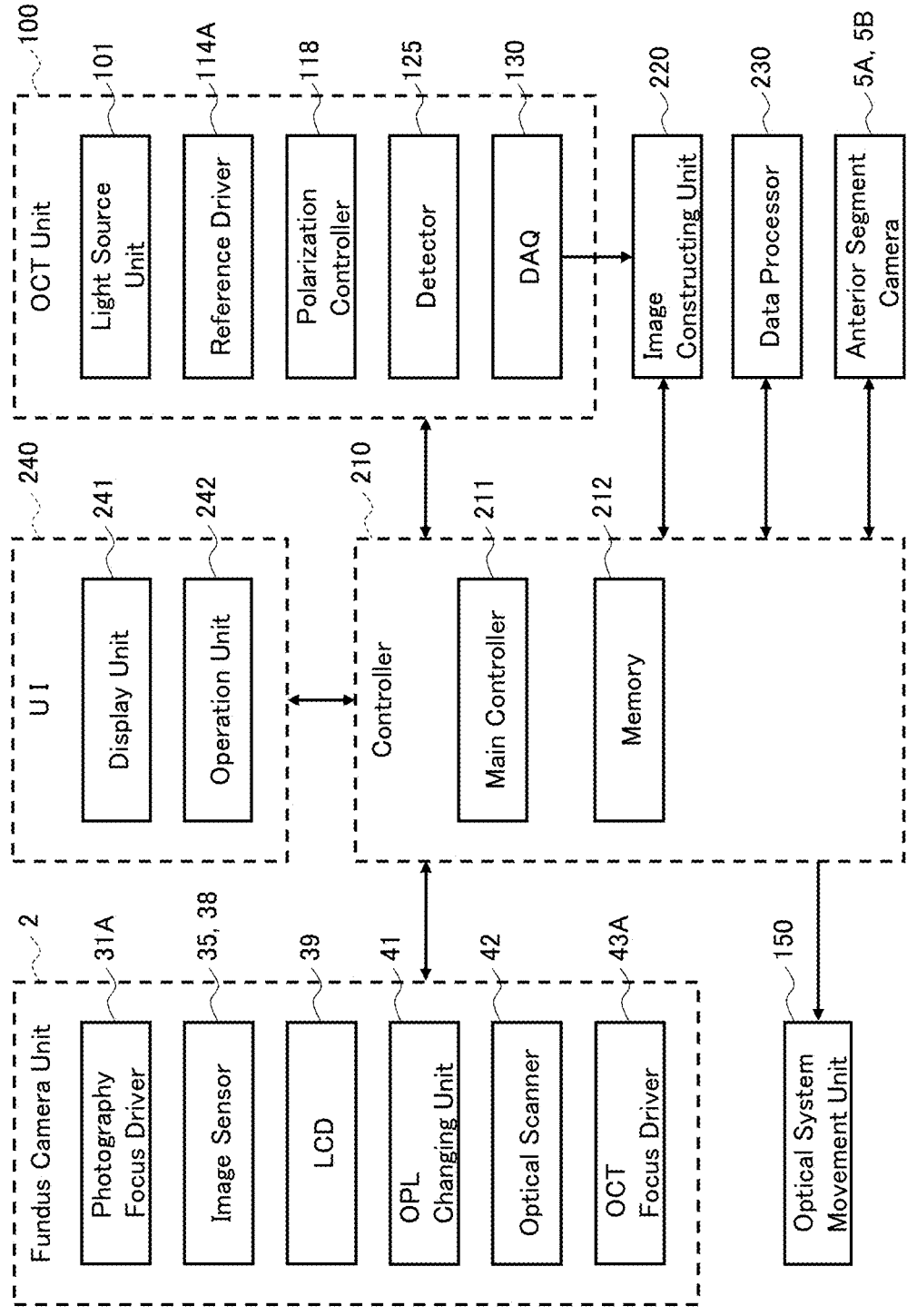
FIG. 10 is a schematic diagram showing an example of the configuration of the ophthalmic apparatus according to an embodiment example.

FIG. 10 show an example of the configuration of the control system of the ophthalmic apparatus 1. The controller 210, the image constructing unit 220 and the data processor 230 are provided in the arithmetic and control unit 200.

The controller 210 performs various kinds of controls. The controller 210 includes the main controller 211 and the memory 212. The controller 210 includes a processor.

The main controller 211 controls each element (each unit, each part, each section, etc.) of the ophthalmic apparatus 1 (including the elements shown in FIG. 8 to FIG. 10). The photography focus driver 31A shown in FIG. 10 moves the photography focusing lens 31, the OCT focus driver 43A moves the OCT focusing lens 43, and the reference driver 114A moves the corner cube 114.

The optical system movement unit 150 moves at least part of the optical system provided in the ophthalmic apparatus 1. As a typical example, the optical system movement unit 150 is configured to move the fundus camera unit 2 in a three dimensional manner. In this case, the optical system movement unit 150 includes the followings, for example: one or more movable tables on which the fundus camera unit 2 is mounted; and one or more actuators for moving the one or more movable tables in the lateral direction (i.e., the left and right direction, or the x direction), an up and down direction (i.e., the y direction), and a front-back direction (i.e., the direction along the optical axis of the objective lens, or the z direction).

The memory 212 stores various kinds of data. Examples of the data stored in the memory 212 include OCT images, anterior segment images, fundus images, and subject's eye information. The subject's eye information includes subject information such as the patient ID and the patient's name, identification information for the left eye and the right eye, and electronic medical record information. Further, the memory 212 stores information indicating a standard depth level set in advance. The standard depth level may be set in the manner as described above.

The image constructing unit 220 constructs an image based on an output from the DAQ 130 (i.e., based on a result obtained by the sampling of detection signals). For example, the image constructing unit 220 generates a reflection intensity profile for each A-line by applying signal processing to the spectral distribution formed from the sampling result for each A-line in the same manner as in the conventional swept source OCT techniques. Such a reflection intensity profile thus generated is referred to as an A-scan, an A-scan image, or the like. This signal processing includes, for example, noise elimination (or noise reduction), filtering, and fast Fourier transform (FFT), etc. Further, the image constructing unit 220 performs image processing on a plurality of A-line profiles respectively corresponding to the plurality of A-lines and arranges the resulting images according to the line to which scanning is applied. By so doing, the image constructing unit 220 constructs a cross sectional image according to the arrangement of the plurality of A-lines. Such a cross sectional image is referred to as a B-scan, a B-scan image, or the like. The image constructing unit 220 includes a processor.

The data processor 230 executes various kinds of data processing. As some typical examples, the data processor 230 performs processing of an image (e.g., fundus image, anterior segment image, etc.) acquired by the fundus camera unit 2, processing of an image acquired by the anterior segment cameras 5A and 5B, and processing of an image constructed by the image constructing unit 220. Such processing includes at least one of various kinds of image processing and various kinds of analysis processing. For example, the data processor 230 executes construction of three dimensional image data (e.g., stack data, volume data) from OCT raster scan data, rendering of three dimensional image data, image correction, image analysis according to analysis application software. The data processor 230 includes a processor.

As described above, the ophthalmic apparatus 1 according to the present embodiment example includes the optical path length changing unit 41 for changing the optical path length of the measurement light LS, and the corner cube 114 as well as the reference driver 114A for changing the optical path length of the reference light LR. Generally, at least one of an element for changing the optical path length of the measurement light and an element for changing the optical path length of the reference light may be provided. In other words, an element may be provided for varying the difference between the measurement arm length and the reference arm length.

The ophthalmic apparatus 1 (in particular, the main controller 211 and the data processor 230) controls the optical path length changing unit (e.g., the optical path length changing unit 41 and/or the reference driver 114A) to place partial data of OCT data corresponding to a predetermined part (a predetermined site, a predetermined tissue) of the fundus Ef at a standard depth level set based on a predetermined ocular parameter value and stored in the memory 212 in advance. Typically, the ophthalmic apparatus 1 (in particular, the main controller 211 and the data processor 230) is configured to control the optical path length changing unit 41 and/or the reference driver 114A to regulate the difference between the measurement arm length and the reference arm length, in such a manner that an image region (e.g., an RPE region) corresponding to a predetermined part in an OCT image (e.g., a B-scan image) constructed by the image constructing unit 220 based on data acquired from the subject's eye E (i.e., the fundus Ef) through an OCT scan is placed at a predetermined standard depth level. The ophthalmic apparatus 1 (in particular, the main controller 211 and the data processor 230) includes a processor that operates according to a predetermined optical path length control program. The ocular parameter value used for setting the standard depth level in the present embodiment example may include, for example, at least one of the values of the axial length and the optical power.

The standard depth level is a depth level or depth position (z coordinate) used as a targeted depiction position of a reference site of the subject's eye. The reference site is a predetermined part, site, tissue, or the like of the eye, and may be the retinal pigment epithelium, for example. In the case where an OCT scan is applied to the fundus Ef as in the present embodiment example, the standard depth level may be set such that both edges of a predetermined first eye fundus tissue (e.g., the retinal surface) are not protruded from the image frame. In other words, such a standard depth level may be set in such a way that the edges of the first partial data corresponding to the first eye fundus tissue are placed on the lateral sides of the image frame. In further other words, the standard depth level may be set such that the edges of the first partial data corresponding to the first eye fundus tissue are not placed on the upper edge of the image frame.

Further, the standard depth level may be set based on the second partial data corresponding to a predetermined second eye fundus tissue located at a deeper level than the retinal surface. A typical example of the second eye fundus tissue is the retinal pigment epithelium (RPE). The standard depth level may be set at an average depth level of the second partial data, or may be set at a deeper level than the average depth level of the second partial data, that is, at a level closer to the bottom edge of the image frame with respect to the average depth level.

As described above, the second eye fundus tissue may be set at a level deeper than the first eye fundus tissue by a predetermined distance. The predetermined distance is typically a standard value determined clinically. For example, in the case where the first eye fundus tissue is the retinal surface and the second eye fundus tissue is the retinal pigment epithelium, the second partial data corresponding to the retinal pigment epithelium may be set to be a region determined by shifting the first partial data corresponding to the retinal surface by 0.5 mm toward the lower edge of the image frame. Presetting the distance between the first partial data and the second partial data like this makes it possible to eliminate the necessity of image analysis for detecting the second eye fundus tissue and to reduce resources and time required for analysis of OCT images.

A specific example will be described. First, the data processor 230 analyzes an OCT image constructed by the image constructing unit 220 based on data acquired from the fundus Ef by an OCT scan, to detect an image region (e.g., the ILM region) corresponding to the retinal surface. Next, the data processor 230 sets a region located 0.5 mm deeper than the detected ILM region as the RPE region. Subsequently, the data processor 230 averages the depth levels (z coordinates) of a plurality of points (a plurality of pixels) in the RPE region. Then, the data processor 230 compares the calculated average depth level (the average z coordinate of the RPE region) with the standard depth level stored in the memory 212, thereby calculating the deviation of the average depth level with respect to the standard depth level. For example, the data processor 230 transmits, to the main controller 211, control information including the calculated deviation or control information including the amount of change in the measurement arm length and/or the reference arm length for compensating the calculated deviation. Based on the control information sent from the data processor 230, the main controller 211 controls the optical path length changing unit 41 and/or the reference driver 114A to change the measurement arm length and/or the reference arm length in a direction and by a distance that compensate the deviation of the average depth level with respect to the standard depth level.

By repeating such a series of processes, the Auto-Z and the Z-lock may be carried out. The Auto-Z is an automatic operation for placing the average depth level of the RPE region at the standard depth level, and the Z-lock is an automatic operation for maintaining the state in which the average depth level of the RPE region is located at the standard depth level. Further, by setting the standard depth level as described above, the image of the retinal surface does not protrude from the upper edge of the image frame and an OCT image of the fundus Ef can be obtained in which no fold-over artifact is mixed.

The user interface (UI) 240 includes the display unit 241 and the operation unit 242. The display unit 241 includes the display device 3. The operation unit 242 includes various operation devices and input devices. The user interface 240 may include, for example, a device having both a display function and an operation function, such as a touch panel. Other embodiment examples may not include at least part of the user interface 240. For example, the display device may be an external device connected to the ophthalmic apparatus.

<Another Embodiment Examples>

An ophthalmic apparatus according to another embodiment example will be described. The present aspect example realizes optical path length adjustment on the basis of an ocular characteristic value of the subject's eye.

The ocular characteristic value of the subject's eye may be, for example, any of the above-mentioned ocular parameter values or any parameter value substantially equivalent to an ocular parameter value. Here, substantial equivalence of two parameter values means, for example, that the two parameter values are mutually convertible or exchangeable by a predetermined operation. More generally, the substantial equivalence means that one of the two parameter values can be derived from the other by a predetermined operation. The ocular characteristic value of the subject's eye may be a value obtained by actually measuring the subject's eye (i.e., measured value), or a value obtained by estimation from predetermined conditions or predetermined information (i.e., estimated value).

The ophthalmic apparatus according to the present embodiment example has the same functions and configurations as the ophthalmic apparatus according to the above-described aspect example, and is capable of performing optical path length control (that is, the control of the measurement arm length and/or the control of the reference arm length) to place partial data of OCT data corresponding to a predetermined part (site, tissue) of an eye at the standard depth level set based on a predetermined ocular parameter value.

Figure 11:
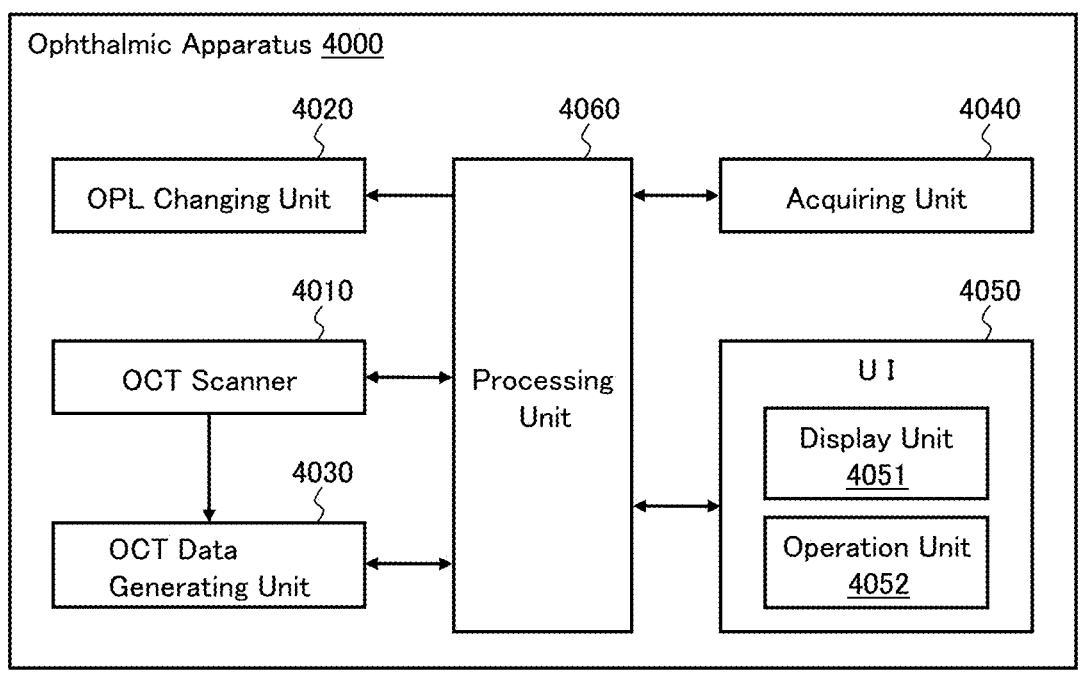
FIG. 11 is a schematic diagram showing an example of the configuration of the ophthalmic apparatus according to another embodiment example.
Figure 12:
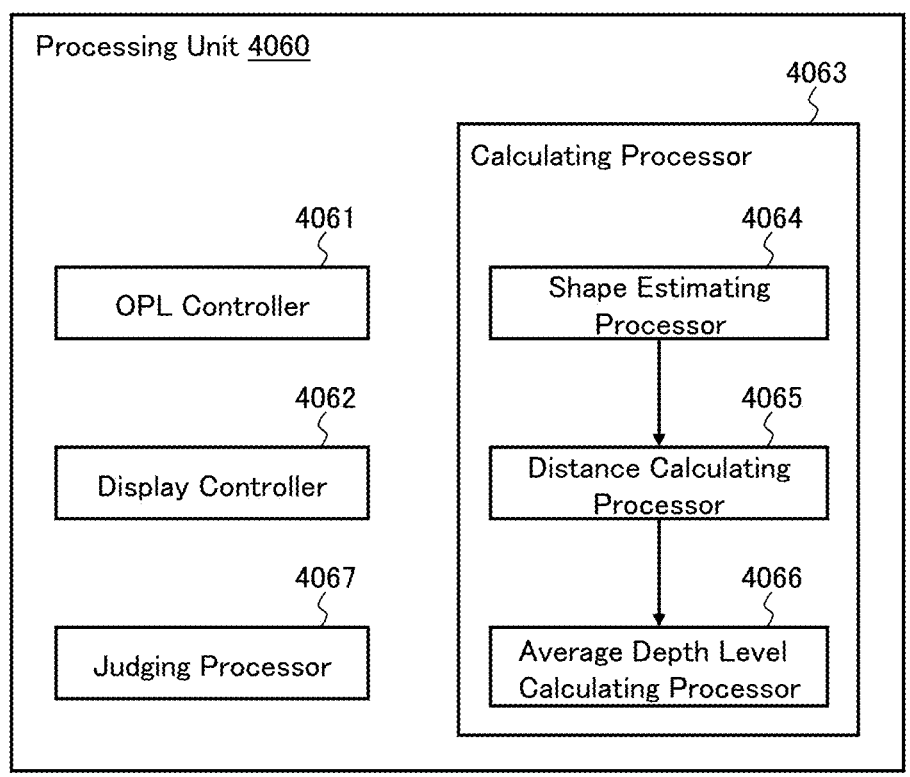
FIG. 12 is a schematic diagram showing an example of the configuration of the ophthalmic apparatus according to another embodiment example.

FIG. 11 and FIG. 12 show configuration examples of the ophthalmic apparatus according to the present embodiment example. The ophthalmic apparatus 4000 includes the OCT scanner 4010, the optical path length changing unit 4020 (OPL changing unit 4020), the OCT data generating unit 4030, the acquiring unit 4040, the user interface (UI) 4050, and the processing unit 4060.

The OCT scanner 4010 includes an interferometer that includes a measurement arm and a reference arm. The measurement arm includes an optical scanner such as a galvano mirror scanner and carries out various kinds of scan modes such as B-scan and three dimensional scan. The optical path length changing unit 4020 includes either one or both of a mechanism for changing the measurement arm length and a mechanism for changing the reference arm length. The OCT data generating unit 4030 is configured to generate OCT data based on an output from the OCT scanner 4010.

The acquiring unit 4040 is configured to acquire an ocular characteristic value of the subject's eye. The ocular characteristic value may be, for example, an equivalent spherical power (spherical equivalent), a spherical power, an axial length, or a parameter value equivalent to any of these. The acquiring unit 4040 may include, for example, any of the following optional configurations: (the first optional configuration) a configuration that receives an input of an ocular characteristic value of the subject's eye obtained in a past measurement; (the second optional configuration) a configuration that measures an ocular characteristic value of the subject's eye; (the third optional configuration) a configuration that estimates an ocular characteristic value of the subject's eye from the states or conditions of elements of the ophthalmic apparatus 4000.

The user interface 4050 is a man-machine interface for exchanging information between the ophthalmic apparatus 4000 and the user. The user interface 4050 includes the display unit 4051 and the operation unit 4052.

The processing unit 4060 includes a processor configured and programmed to execute information processing according to a program. In particular, the processing unit 4060 executes the above-mentioned optical path length control based on the ocular characteristic value of the subject's eye acquired by the acquiring unit 4040. More specifically, the processing unit 4060 performs, based on the ocular characteristic value of the subject's eye acquired by the acquiring unit 4040, the optical path length control to place the partial data of the OCT data corresponding to a predetermined part of the eye at the standard depth level set based on a predetermined ocular parameter value. Here, the optical path length control includes at least one of the control of the measurement arm length and the control of the reference arm length.

The processing unit 4060 may be configured to perform the optical path length control such that an edge of partial data (third partial data) corresponding to a predetermined eye fundus tissue (third eye fundus tissue) is placed on a lateral side of an image frame. Further, the processing unit 4060 may be configured to perform the optical path length control based on partial data (fourth partial data) corresponding to a predetermined eye fundus tissue (fourth eye fundus tissue) located at a deeper level than the third eye fundus tissue.

The third eye fundus tissue may be, for example, a retinal surface (inner limiting membrane, ILM), and the fourth eye fundus tissue may be, for example, a retinal pigment epithelium (RPE). Hereinafter, it is assumed that the third eye fundus tissue is the retinal surface and the fourth eye fundus tissue is the RPE.

In the case where the ophthalmic apparatus 4000 employs the configuration of the above-described embodiment example (the configuration of the ophthalmic apparatus 1), each element of the ophthalmic apparatus 4000 may be implemented by using under-mentioned elements of the ophthalmic apparatus 1. That is, elements of the ophthalmic apparatus 4000 and elements of the ophthalmic apparatus 1 have the following correspondence.

First, the OCT scanner 4010 includes the OCT unit 100 and the elements (optical elements etc.) in the fundus camera unit 2 that form the measurement arm. The optical path length changing unit 4020 includes at least one of the optical path length changing unit 41 for changing the measurement arm length, and the combination of the corner cube 114 and the reference driver 114A for changing the reference arm length. The OCT data generating unit 4030 includes the image constructing unit 220.

Further, the acquiring unit 4040 (the first optional configuration) includes any of the followings; the user interface 240 (e.g., in the case of manually inputting an ocular characteristic value); a communication device (not shown in the drawings) (e.g., in the case of receiving an ocular characteristic value transmitted from another ophthalmic apparatus or an external device); and a drive device (not shown in the drawings) (e.g., in the case of reading an ocular characteristic value recorded on a recording medium). The second optional configuration and the third optional configuration will be described later.

The user interface (UI) 4050 includes the user interface 240. The display unit 4051 includes the display unit 241. The operation unit 4052 includes the operation unit 242. The processing unit 4060 includes the main controller 211 and the data processor 230.

Some examples of the acquiring unit 4040 will be described. In the case of employing the first optional configuration that receives the input of the ocular characteristic value of the subject's eye obtained in the past measurement, the acquiring unit 4040 includes a communication device that operates under the control of the processing unit 4060, and receives, with the communication device, the ocular characteristic value of the subject's eye externally transferred. For example, the ophthalmic apparatus 4000 may access an electronic medical record system by using the acquiring unit 4040, and retrieve and acquire the ocular characteristic value from the electronic medical record of the subject. The communication device may have a communication function via a local area network (LAN), a communication function via a wide area network (WAN), a communication function via a dedicated line, and the like.

In the case of employing the second optional configuration that measures the ocular characteristic value of the subject's eye, the acquiring unit 4040 has, for example, a function of an eye optical power measurement apparatus such as refractometer. For example, the apparatus disclosed in Japanese Unexamined Patent Application Publication No. 2017-192828 is known as an ophthalmic apparatus that is a combination of an OCT apparatus and a refractometer. The acquiring unit 4040 of the second optional configuration may include the followings, for example: an optical system configured to project a light beam having a ring-shaped cross section onto the fundus of the subject's eye; an optical system configured to detect return light of the light beam projected; and a processor configured and programmed to analyze the result of the detection of the return light to determine an ocular characteristic value. In another example, the acquiring unit 4040 of the second optional configuration may include the followings: an optical system configured to project a light beam onto the fundus of the subject's eye; an optical system configured to convert the return light of the light beam into a light beam having a ring-shaped cross section, and to detect the light beam having a ring-shaped cross section; and a processor configured and programmed to analyze the result of the detection of the light beam having a ring-shaped cross section to determine an ocular characteristic value. The processor may be configured and programmed to calculate a spherical power from the detection result. The processor may be configured and programmed to calculate a spherical power and an astigmatic power, and then calculate an equivalent spherical power from the spherical power and the astigmatic power.

In some other examples of the second optional configuration, the acquiring unit 4040 has a function of an axial length measurement apparatus. The axial length measurement utilizes OCT techniques or ultrasonic measurement techniques, for example. A method, technique, and configuration for the axial length measurement using OCT techniques are disclosed in Japanese Unexamined Patent Application Publication No. 2017-192828, for example. A method, technique, and configuration for the axial length measurement using ultrasonic measurement techniques are disclosed in International Publication No. WO 2013/002332, for example.

In the case of employing the third optional configuration that estimates an ocular characteristic value of the subject's eye from the states of elements of the ophthalmic apparatus 4000, the acquiring unit 4040 may use, for example, the result of focus adjustment of the optical system of the ophthalmic apparatus 4000 with respect to the subjects eye. In the case of employing the configuration of the ophthalmic apparatus 1 according to the above-described embodiment example, the acquiring unit 4040 may be configured to estimate the optical power of the subject's eye based on any of the following pieces of information: position information of the OCT focusing lens 43; position information of the photography focusing lens 31; control information of the OCT focus driver 43A; and control information of the photography focus driver 31A. In addition, the acquiring unit 4040 may be configured to estimate the optical power of the subjects eye by further referring to the fact whether or not the diopter correction lenses 70 and 71 are used.

Some examples of the processing unit 4060 will be described. FIG. 12 shows a configuration example of the processing unit 4060. The processing unit 4060 of the present example includes the optical path length controller 4061 (OPL controller 4061), the display controller 4062, the calculating processor 4063, and the judging processor 4067.

The optical path length controller 4061 is configured and programmed to control the optical path length changing unit 4020. The display controller 4062 is configured and programmed to control the display unit 4051.

The calculating processor 4063 is configured and programmed to calculate the average depth level of the image region (the RPE region) corresponding to the RPE based on the ocular characteristic value of the subject's eye acquired by the acquiring unit 4040. The average depth level calculation is executed according to a predetermined algorithm. The algorithm may be formulated based on, but not limited to, the methods described in the aspect examples above.

Rather than performing the calculation based on OCT data acquired from the subject's eye, the calculating processor 4063 performs a simulation using the ocular characteristic value (and a predetermined ocular parameter value) of the subject's eye to estimate the average depth level of the RPE. Therefore, the eye fundus tissue (e.g., the retinal surface, the ILM, the RPE, etc.) in the present example may not be an actual eye fundus tissue (a real tissue of an eye) but a virtual eye fundus tissue in a simulation model. Similarly, the image region (e.g., the ILM region, the RPE region, etc.) in the present example may not be partial data of an actual OCT image (partial data of an OCT image of an eye) but a virtual image region in a simulation model.

The simulation executed by the calculating processor 4063 uses one or more predetermined ocular parameter values. Such an ocular parameter value may be a standard value derived clinically (e.g., derived using statistical calculation), or may be a measured value obtained from the subject's eye or another eye. The standard value of an ocular parameter may be a single value considered to be the most standard for that ocular parameter, or may be two or more values different from each other. In the latter case, one value corresponding to an attribute of the subject's eye and/or an attribute of the subject is selected from the two or more values and used for the simulation. Examples of the attributes include age, sex, race, region, medical history, family history, ophthalmic examination data, and examination data from a medical field other than ophthalmology.

The simulation of the present embodiment example mainly uses the parameter value(s) of the above-described aspect example. For example, the simulation employs the following conditions: the distance between the retinal surface and the RPE is assumed to be 0.5 mm (500 μm); the distance between the pivot point of the OCT measurement light and the corneal apex is assumed to be 1.82 mm; the axial length corresponding to the optical power 0 D is assumed to be 24 mm; the axial length is assumed to extend by ⅓ mm each time the optical power decreases by 1 D (that is, every time the degree of myopia increases by 1 D); the focal length of the eye is assumed to be 17 mm; the OCT scan mode is assumed to be a B-scan with the line length of 12 mm; and the maximum deflection angle of the OCT measurement light corresponding to the eye focal length of 17 mm and the OCT scan size of 12 mm is assumed to be 19.44 degrees.

These parameter values are merely examples, and other values may be employed instead. Further, as described above, two or more values may be prepared for a certain parameter and used in a selective manner. One example prepares four values 6 mm, 9 mm, 12 mm, and 15 mm for the OCT scan size (the line length of a B-scan), and also prepares four maximum deflection angles of the OCT measurement light respectively corresponding to the four OCT scan sizes. The relationship between the OCT scan sizes and the maximum deflection angles is not limited to such a discrete relationship, and may be a continuous relationship represented by a graph or the like.

Furthermore, the standard depth level is set in advance according to the specifications of the ophthalmic apparatus 4000 (an OCT apparatus). For example, referring to the aspect example described above, the standard depth level may be set at a position of the 450th pixel from the upper edge of the image frame in the case where the number of pixels from the upper edge to the lower edge of the image frame (the number of pixels arrayed in the depth direction (the z direction)) is 992, and where the resolution in the depth direction is 2.6 um/pixel.

The optical path length controller 4061 may control the optical path length changing unit 4020 based on the average depth level of the RPE region calculated by the calculating processor 4063 and the standard depth level set in advance. This optical path length control is referred to as the first control. As in the aspect example described above, the optical path length controller 4061 may carry out the first control in such a manner that the average depth level of the RPE region is placed at the standard depth level. In other words, the optical path length controller 4061 may carry out the first control in such a manner that the average depth level of the RPE region matches with the standard depth level. The first control may be actually-performed control for the optical path length changing unit 4020, or a virtually-performed optical path length change as a simulation.

In an example for implementing the algorithm based on the aspect example described above, the calculating processor 4063 may be configured to perform a process of estimating the shape of the RPE region of the subject's eye, and a process of calculating an average depth level of the RPE region based on the shape estimated. In addition to this, the calculating processor 4063 may be configured to set the level of the third partial data corresponding to the retinal surface to a level shallower than the fourth partial data corresponding to the RPE by a predetermined distance.

In a further example, the calculating processor 4063 may be configured to perform the following processes: a process of estimating the shape of the RPE of the subject's eye; a process of determining a distance distribution between the pivot position of the OCT scanning and the estimate shape of the RPE (that is, the estimate shape (estimated location, estimated distribution) of the RPE region); and a process of obtaining the average depth level of the RPE region based on the distance distribution determined.

The exemplary calculating processor 4063 for implementing such an operation and calculation includes the shape estimating processor 4064, the distance calculating processor 4065, and the average depth level calculating processor 4066.

The shape estimating processor 4064 is configured and programmed to estimate the shape of the RPE of the subject's eye based on the ocular characteristic value of the subject's eye acquired by the acquiring unit 4040. The RPE shape estimation may be performed using an arbitrary calculation (operation) technique, and is typically performed using an arbitrary simulation.

As an example, the estimate shape of the RPE of the subject's eye may be obtained by substituting the optical power (e.g., the equivalent spherical power) of the subject's eye acquired by the acquiring unit 4040 into the relationships (equations) "Rz (mm)=−0.163 D+10.148, Rx (mm)=−0.043 D+11.455, Ry (mm)=−0.090 D+11.365" presented in the following document described in the aspect example described above: David A. Atchison et al., "Shape of the Retinal Surface in Emmetropia and Myopia", Investigative Ophthalmology & Visual Science, August 2005, Vol. 46, No. 8, PP. 2698-2707. Such calculation may yields an eye model constructed with taking into account the ocular characteristic value of the subject's eye.

The distance calculating processor 4065 is configured and programmed to determine a distance distribution between the pivot position of the OCT scanning and the estimate shape of the RPE obtained by the shape estimating processor 4064 (see FIG. 7A and the description thereon). For example, the distance calculating processor 4065 first sets the pivot position of the OCT measurement light in the eye model based on the estimate shape of the RPE obtained by the shape estimating processor 4064. The pivot position setting is carried out on the basis of the aforementioned parameter value (note that the distance between the pivot point and the corneal apex is assumed to be 1.82 mm). More specifically, the present example sets (places) the pivot position in the eye model at a position separated from the corneal apex in the depth direction by 1.82 mm.

Next, the distance calculating processor 4065 calculates the distance between the pivot position set in the eye model and each of a plurality of positions in the eye model corresponding to the RPE. This gives a distance distribution between the pivot position and the estimated RPE.

Note that the plurality of positions on the estimated RPE used for deriving the distance distribution is set in an optional manner. For example, the plurality of positions may be set on the estimated RPE at equal intervals. Another example may be configured to calculate the distances from the pivot position for a plurality of positions including: the position on the estimated RPE at which the virtual ray corresponding to the maximum deflection angle intersects the estimated RPE; and the deepest position of the estimated RPE.

The average depth level calculating processor 4066 is configured and programmed to calculate the average depth level of the RPE, based on the distance distribution between the pivot position obtained by the distance calculating processor 4065 and the estimated RPE (the estimate shape of RPE). Some typical examples of the average depth level calculation include a calculation of determining the average value of a plurality of values included in the distance distribution. Some other examples may determine the average depth level by performing a weighted average calculation on a plurality of values included in the distance distribution.

The optical path length controller 4061 may perform the above-described first control for the optical path length changing unit 4020 based on the average depth level of the RPE calculated by the average depth level calculating processor 4066 and the standard depth level. For example, the optical path length controller 4061 may perform the first control for the optical path length changing unit 4020 such that the average depth level of the RPE calculated by the average depth level calculating processor 4066 is placed at the standard depth level. That is, the optical path length controller 4061 may perform the first control for the optical path length changing unit 4020 in such a manner that the average depth level becomes equal to the standard depth level.

It can be said that performing such optical path length adjustment improves the possibility that the edges of the retinal surface image is located on the lateral sides of the image frame if the shape, size, and retinal thickness of the subjects eye are standard. That is, as long as the shape, size, and the retinal thickness of the subject's eye do not deviate from their standard ranges (defined based on the optical power of the subject's eye), the retinal surface image does not protrude from the upper edge of the image frame, and a fundus OCT image is obtained in which no fold-over artifact is mixed.

However, considering that the optical path length adjustment in the present example is performed focusing on the RPE, there is some possibility that the retinal surface image depicted at a level shallower than the RPE image may protrude from the upper edge of the image frame. The judging processor 4067 may be provided to cope with such an inconvenience.

The judging processor 4067 is configured and programmed to judge whether the edge of the retinal surface (an estimated retinal surface, an ILM region) is located on the lateral side of the image frame.

To perform such a judgment process, first, the judging processor 4067 determines and sets an estimated retinal surface in the eye model created based on the optical power of the subject's eye. More specifically, the judging processor 4067 determines and sets the estimated retinal surface in a location shallower, by a predetermined distance, than the estimated RPE obtained by the calculating processor 4063 (the shape estimating processor 4064). The present example may set the estimated retinal surface in the eye model to be a region shallower than the estimated RPE by 0.5 mm (that is, a region closer to the corneal apex than the estimated RPE by 0.5 mm). This estimated retinal surface setting is executed based on the above-mentioned parameter value (note that the distance between the retinal surface and the RPE is assumed to be 0.5 mm).

Next, the judging processor 4067 determines depth level coordinates (z coordinates) of a plurality of positions on the estimated retinal surface. Furthermore, the judging processor 4067 judges whether a negative value is included in the z coordinates determined. In other words, the judging processor 4067 carries out the judgment whether any position of the estimated retinal surface is located above the upper edge of the image frame. If there are one or more positions where the signs of their z coordinates are negative, a fold-over artifact may occurs.

Generally, the shape of the (estimated) retinal surface is convex downward (convex toward +z direction), and the z coordinate of the edge of the retinal surface is the smallest among the z coordinates of the retinal surface. Therefore, the z coordinate value of the edge of the retinal surface is most likely to be negative. Taking such knowledge into account, the judging processor 4067 may be configured to conduct the judgment whether or not the sign of a z coordinate value is negative, only for the edge of the retinal surface. It is sufficient for the present example to conduct the judgment whether or not the z coordinate of the retinal surface has a negative value, only for the position corresponding to the edge of the OCT scan size of 12 mm included in the above parameter values.

Further optical path length adjustment may be performed based on the result of the judgment executed by the judging processor 4067. For example, such further optical path length adjustment may be performed to shift the image of the subjects eye relatively downward with respect to the image frame if the judging processor 4067 judges that the retinal surface protrudes from the upper edge of the image frame after the first control.

As an example, the optical path length controller 4061 may be configured to control the optical path length changing unit 4020 such that the average depth level of the RPE is placed at a level deeper than the standard depth level if the judging processor 4067 judges that the edge of the retinal surface is not located on the lateral side of the image frame after the first control. Such optical path length control is referred to as the second control. The second control may be an actually-performed control for the optical path length changing unit 4020 or a virtually-performed optical path length change as a simulation.

The second control may be executed in such a manner that the average depth level of the RPE is placed at a level below the standard depth level by a predetermined distance (e.g., 100 pixels), for example. Alternatively, the second control may include a process of determining a deviation distance, and a process of shifting the average depth level of the RPE to a level below the standard depth level by the deviation distance determined. For example, the deviation distance may be determined based on the level of the retinal surface in the depth direction. Typically, the deviation distance may be determined such that the z coordinate, which is a negative value, of the edge of the retinal surface after the first control becomes zero or a positive value. As a specific example, the second control may be performed such that the average depth level of the RPE is placed below the standard depth level by K pixels in the case where the edge of the retinal surface after the first control is located above the upper edge of the image frame by k pixels (where K≥k).

In another example, the size of the image frame in the up and down direction may be enlarged if the judging processor 4067 judges that the edge of the retinal surface is not located on the lateral side of the image frame after the first control. In particular, the enlargement of the image frame may be conducted so as to move the upper edge of the image frame to a higher level. In this way, the imaging area in the depth direction may be enlarged.

The judging processor 4067 may perform re-judgment regarding whether or not the edge of the retinal surface is placed on the lateral side of the image frame after the second control. Such re-judgment makes it possible to check whether the entire retinal surface is depicted in the image frame by the second control.

The processing unit 4060 (in particular, the optical path length controller 4061 and the judging processor 4067) may be configured to repeat the control of the optical path length changing unit 4020 for (sequentially) shifting the average depth level of the RPE to a deeper level until the judging processor 4067 judges that the edge of the retinal surface is located on the lateral side of the image frame. With this, the optical path length adjustment may be performed such that the entire retinal surface is depicted in the image frame.

An example of the operation of the ophthalmic apparatus 4000 will be described with reference to FIG. 13. The operation shown in the flowchart of FIG. 13 is executed after preliminary operations such as registration of a patient ID.

First, the acquiring unit 4040 acquires the ocular characteristic value of the subject's eye (S1). The processing unit 4060 reads out the above-mentioned parameter value from a storage device (not shown in the drawings), and sets the parameter value for the subsequent processing (S2).

Next, the shape estimating processor 4064 determines the estimate shape of the retinal pigment epithelium (the estimated RPE), based on the ocular characteristic value acquired in the step S1 (S3). The calculating processor 4063 may create an eye model, based on the estimated RPE determined in the step S3 and on the parameter value obtained in the step S2.

Then, the distance calculating processor 4065 determines a distance distribution between the pivot position and the estimated RPE, based on the information of the pivot position included in the parameter value obtained in the step S2 (the pivot position of the OCT scanning) and on the estimate shape of the RPE determined in the step S3 (S4).

After that, the average depth level calculating processor 4066 determines the average depth level of the estimated RPE, based on the distance distribution obtained in the step S4 (S5).

Subsequently, the processing unit 4060 assigns the average depth level set in the step S5 to the default setting of the standard depth level (e.g., a position of 450 pixels below the upper edge of the image frame) (S6).

Next, the judging processor 4067 sets the estimated retinal surface at a position shallower than the estimated RPE obtained in the step S3 by a predetermined distance. Further, the judging processor 4067 determines the depth level coordinates (the z coordinates) of a plurality of positions on the estimated retinal surface set at the above position (S7).

Next, the judging processor 4067 judges whether or not a negative value is included in the z coordinates obtained for the plurality of positions on the estimated retinal surface in the step S7 (S8). If the judging processor 4067 judges that a negative z coordinate exists (S8: Yes), the process proceeds to the step S9. On the other hand, if the judging processor 4067 judges that no negative z coordinate exists (S8: No), the process proceeds to the step S10.

If the judging processor 4067 judges that one or more negative z coordinates exist (S8: Yes), the processing unit 4060 shifts the average depth level of the estimated RPE downward (S9). That is, the processing unit 4060 performs the optical path length adjustment such that the average depth level of the estimated RPE is displaced to a level deeper than the current depth level. Note that the current depth level is the preset standard depth level at this stage. Such optical path length adjustment is typically an optical path length shift as a simulation, and does not need to conduct actual change in optical path length.

After the optical path length shift (the downward shift of the average depth level) in the step S9, the judgment in the step S8 is performed again. That is, the judging processor 4067 judges whether or not a negative value is included in the z coordinates of the estimated retinal surface after the optical path length shift (S8). The steps S8 and S9 are repeated until the judgment result becomes "No" in the step S8. By this repetition (iteration) of the processes, an appropriate standard depth level may be attained at which the estimated retinal surface does not protrude from the upper edge of the image frame.

If the judgment result is "No" in the step S8, the processing unit 4060 sets the average depth level of the RPE at this stage, to the (initial) standard depth level to be applied in OCT scanning for the subjects eye (S10). Here, the optical path length controller 4061 controls the optical path length changing unit 4020 such that the initial standard depth level is realized.

At this stage, the ophthalmic apparatus 4000 may perform preliminary operations for OCT scanning, such as alignment and focus adjustment.

The processing unit 4060 applies OCT scanning to the fundus of the subject's eye by using the OCT scanner 4010 (S11). For example, the processing unit 4060 applies an OCT scan having the pattern and size set in the step S2 (e.g., the B-scan with the line length of 12 mm) to the fundus of the subject's eye. The OCT data generating unit 4030 generates OCT data based on the data acquired by the OCT scanner 4010 (S11). The display controller 4062 displays an OCT image constructed based on the OCT data generated, on the display unit 4051 (S11).

The processing unit 4060 (e.g., the optical path length controller 4061) may perform control for the optical path length changing unit 4020, based on the OCT data obtained in the step S11 (S12). Here, the control for the optical path length changing unit 4020 may include regulating the depth range to which OCT scanning and imaging processing are applied, and/or regulating the depth level of the image. The optical path length control may be either automatic control based on analysis of OCT data or manual control based on user instructions. In the case of the automatic control, displaying the OCT image in the step S11 is not necessary.

Some examples of the automatic control will be described. In the first example of the automatic control, the processing unit 4060 is configured to judge whether or not the OCT data generated in the step S11 contains a fold-over artifact corresponding to the retinal surface (and/or another site). The detection of the fold-over artifact is carried out by any known image processing for artifact detection. If a fold-over artifact is detected, the processing unit 4060 calculates the optical path length change amount for eliminating the fold-over artifact. The optical path length change amount here is a relative downward shift amount of the fundus image with respect to the image frame. The optical path length controller 4061 controls the optical path length changing unit 4020 to change the optical path length by the optical path length change amount calculated. Such optical path length control is referred to as the third control.

In the second example of the automatic control, the processing unit 4060 detects the image of the retinal surface (and/or another site) depicted in the OCT data generated in the step S11. For example, the processing unit 4060 applies segmentation to the OCT data and detects an ILM region. Further, the processing unit 4060 may judge whether or not the edge of the detected ILM region is located on the lateral side of the image frame. If the edge of the ILM region is not located on the lateral side of the image frame, that is, if the edge of the ILM region is located on the upper edge of the image frame, the processing unit 4060 calculates an optical path length change amount to shift the edge of the ILM region currently located on the upper edge of the image frame to the lateral side of the image frame. Here, the optical path length change amount is the amount of a relative downward shift of the fundus image with respect to the image frame. The optical path length controller 4061 controls the optical path length changing unit 4020 to change the optical path length by the optical path length change amount calculated. This optical path length control is referred to as the third control.

An example of the manual control will be described. In the case of the manual control, the OCT image is displayed on the display unit 4051 in the step S11. The user may input an instruction to the ophthalmic apparatus 4000 by operating the operation unit 4052. The user can check whether or not a fold-over artifact is mixed in the OCT image displayed. In addition, the user can grasp where in the image frame the retinal surface image depicted in the OCT image displayed intersects. If a fold-over artifact is mixed in the OCT image, the user can perform an optical path length changing operation for eliminating the fold-over artifact. Alternatively, in the case where the retinal surface image intersects the upper edge of the image frame, the user can perform an optical path length changing operation for making the retinal surface image to intersect the lateral side of the image frame. The optical path length controller 4061 may control the optical path length changing unit 4020 based on the output from the operation unit 4052 in response to the instruction by the user. Such optical path length control is referred to as the fourth control.

The standard depth level as a default setting applied in the step S6 may be variable. For example, the default standard depth level may be changed according to the size of an OCT scan applied to the subject's eye. Such a condition may be employed in consideration of: the fact or knowledge that a general retinal surface shape is a bowl shape with convex downward; and the fact or knowledge that the distance between the uppermost part (the uppermost edge) and the lowermost part (the deepest part) of the retinal surface becomes longer as the size of an OCT scan (e.g., the line length of the B-scan) becomes larger. In the present example, information indicating the (discrete or continuous) relationship between scan sizes and default standard depth levels may be prepared, and an appropriate default standard depth level may be determined according to a scan size employed. In general, the larger the scan size becomes, the deeper the default standard depth level is set. The information indicating the relationship between scan sizes and default standard depth levels may be created, for example, using the methods and techniques according to the aspect examples described above.

Some modifications may be configured to analytically determine the depth level of the RPE so that the z coordinate of the edge of the retinal surface does not become a negative value. For example, the depth level (e.g., the average depth level) of the RPE may be determined such that the z coordinate of the edge of the retinal surface does not have a negative value, based on the distance distribution obtained by the distance calculating processor 4065. As a result of this, the depth level of the RPE can be determined without having to repeat the processes shown in the steps S8 and S9.

<Control Method, Program, Recording Medium>

The control method of the ophthalmic apparatus according to the aspect example will be described. The ophthalmic apparatus to which the control method is applicable includes an interferometer, an optical path length changing unit, and a processor, and the ophthalmic apparatus applies OCT to a subject's eye. The interferometer includes a measurement arm and a reference arm, and the optical path length changing unit is configured to change at least one of the optical path length of the measurement arm and the optical path length of the reference arm. Examples of such an ophthalmic apparatus include the ophthalmic apparatus 1 and the ophthalmic apparatus 1000 described above. The control method according to the aspect example controls the processor to generate OCT data based on an output from the interferometer. Furthermore, the control method according to the aspect example controls the optical path length changing unit to place partial data of the OCT data corresponding to a predetermined part of the eye at a standard depth level set based on a predetermined ocular parameter value.

Any of the items and matters described regarding the ophthalmic apparatuses according to the aspect examples may be combined with the control method according to the aspect example.

Some aspect examples may provide a program that causes a computer to execute the control method according to the aspect example described above. Any of the items and matters described regarding the ophthalmic apparatuses according to the aspect examples may be combined with the program.

Some aspect examples may provide a computer-readable non-transitory recording medium storing the program described above. Any of the items and matters described regarding the ophthalmic apparatuses according to the aspect examples may be combined with the recording medium. The non-transitory recording medium may be in any form, examples of which include a magnetic disk, an optical disk, a magneto-optical disk, and a semiconductor memory.

According to the control method, the program, or the recording medium according to the aspect example, the optical path length adjusting and regulating functions for OCT can be improved, similarly to the ophthalmic apparatuses according to the aspect examples.

The aspects and embodiment examples in the present disclosure are merely some examples of the embodiments of the present invention. A person who intends to carry out the present invention may make any modifications (e.g., omissions, substitutions, replacements, additions, etc.) within the scope of the present invention and any modifications by known techniques.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus that applies optical coherence tomography (OCT) to an eye, comprising:
   a display;
   an interferometer that includes a measurement arm and a reference arm;
   an OCT data generating circuit configured to generate OCT data based on an output from the interferometer;
   an optical path length changing unit including an actuator and configured to change at least one of an optical path length of the measurement arm and an optical path length of the reference arm; and
   a processing circuit configured to control the optical path length changing unit to display the OCT data in an image frame on the display such that a first portion of the OCT data corresponding to a predetermined part of the eye is displayed at a depth level in the image frame set based on a line length of a B-scan in the OCT data and based on a predetermined ocular parameter value including at least one of an axial length and an optical power,
   wherein the processing circuit controls the optical path length changing unit to display the OCT data in the image frame on the display such that the first portion of the OCT data is displayed at the depth level in the image frame set based on the line length of the B-scan, based on association between line lengths of B-scans and depth levels, and based on the predetermined ocular parameter value including at least one of the axial length and the optical power, wherein the line lengths of the B-scans and the depth levels in the association are set such that the depth levels increase as the line lengths become longer.

2. The ophthalmic apparatus of claim 1, wherein the depth level is set such that an edge of a first portion of the OCT data corresponding to a predetermined first eye fundus tissue is obtained on a lateral side of the image frame.

3. The ophthalmic apparatus of claim 2, wherein
   the first eye fundus tissue is a retinal surface, and
   the depth level is set based on a second portion of the OCT data corresponding to a predetermined second eye fundus tissue located at a deeper level in the image frame than the retinal surface.

4. The ophthalmic apparatus of claim 3, wherein the depth level is set at an average depth level in the image frame of the second portion of the OCT data or a deeper level in the image frame.

5. The ophthalmic apparatus of claim 4, wherein the second eye fundus tissue is a retinal pigment epithelium.

6. The ophthalmic apparatus of claim 5, wherein the second portion of the OCT data corresponding to the retinal pigment epithelium is set at a level deeper in the image frame than the first portion of the OCT data corresponding to the retinal surface by a predetermined distance.

7. The ophthalmic apparatus of claim 1, further comprising an acquiring circuit configured to acquire an ocular characteristic value of the eye,
   wherein the processing circuit performs control of the optical path length changing unit to display the first portion of the OCT data at the depth level in the image frame, based on the ocular characteristic value.

8. The ophthalmic apparatus of claim 7, wherein the processing circuit performs the control such that an edge of a third portion of the OCT data corresponding to a predetermined third eye fundus tissue is obtained on a lateral side of a frame.

9. The ophthalmic apparatus of claim 8, wherein the processing circuit performs the control based on a fourth portion of the OCT data corresponding to a predetermined fourth eye fundus tissue located at a deeper level in the image frame than the third eye fundus tissue.

10. The ophthalmic apparatus of claim 9, wherein the processing circuit includes a calculating processor configured to calculate an average depth level of the fourth portion of the OCT data in the image frame based on the ocular characteristic value, and performs first control of the optical path length changing unit based on the average depth level in the image frame and the depth level.

11. The ophthalmic apparatus of claim 10, wherein the processing unit performs the first control such that the average depth level is displayed at the depth level in the image frame.

12. The ophthalmic apparatus of claim 11, wherein the processing unit further includes a judging processor configured to judge whether the edge of the portion of the OCT data is located on the lateral side of the image frame.

13. The ophthalmic apparatus of claim 12, wherein the processing circuit performs second control of the optical path length changing unit such that the average depth level is obtained at a level deeper than the depth level if the judging processor judges that the edge is not located on the lateral side after the first control.

14. The ophthalmic apparatus of claim 13, wherein the judging processor performs re-judgement after the second control.

15. The ophthalmic apparatus of claim 14, wherein the processing circuit repeats control of the optical path length changing unit for shifting the average depth level to a deeper level in the image frame until the judging processor judges that the edge is located on the lateral side of the image frame.

16. The ophthalmic apparatus of claim 12, wherein the judging processor sets the third portion of the OCT data to a level in the image frame shallower than the fourth portion of the OCT data by a predetermined distance.

17. The ophthalmic apparatus of claim 10, wherein
the fourth eye fundus tissue is a retinal pigment epithelium, and
the calculating processor includes a shape estimating processor configured to determine an estimate shape of the retinal pigment epithelium based on the ocular characteristic value, and determines the average depth level based on the estimate shape.

18. The ophthalmic apparatus of claim 17, wherein the calculating processor further includes a distance calculating processor configured to determine a distance distribution between a pivot position of OCT scanning and the estimate shape, and determines the average depth level based on the distance distribution.

19. The ophthalmic apparatus of claim 17, wherein the third eye fundus tissue is a retinal surface.

20. The ophthalmic apparatus of claim 7, wherein
the OCT data generating circuit generates the OCT data based on an output from the interferometer acquired after the control of the optical path length changing unit, and
the processing circuit performs third control of the optical path length changing unit based on the OCT data.

21. The ophthalmic apparatus of claim 20, wherein the processing circuit analyzes the OCT data for detecting a fold-over artifact, and performs the third control if the fold-over artifact is detected.

22. The ophthalmic apparatus of claim 20, wherein the processing circuit analyzes the OCT data for detecting a retinal surface image, and performs the third control if an edge of the retinal surface image is located on an upper edge of the image frame.

23. The ophthalmic apparatus of claim 7, further comprising an operation circuit, wherein the OCT data generating circuit generates the OCT data based on an output from the interferometer acquired after the control of the optical path length changing unit, and
the processing circuit includes a display controller configured to control the display to display an OCT image based on the OCT data, and performs fourth control of the optical path length changing unit based on an output from the operation circuit in response to an instruction from a user.

24. The ophthalmic apparatus of claim 1, wherein the processing circuit changes the depth level according to a size of OCT scanning applied to the eye.

25. A method of controlling an ophthalmic apparatus that includes a display, an interferometer, an optical path length changing unit including an actuator, and a processor and applies OCT to an eye, the interferometer including a measurement arm and a reference arm, the optical path length changing unit being configured to change at least one of an optical path length of the measurement arm and an optical path length of the reference arm, the method comprising:
controlling the processor to generate OCT data based on an output from the interferometer;
controlling the optical path length changing unit to display the OCT data in an image frame on the display such that a first portion of the OCT data corresponding to a predetermined part of the eye is displayed at a depth level in the image frame set based on a line length of a B-scan in the OCT data and based on a predetermined ocular parameter value including at least one of an axial length and an optical power;
controlling the optical path length changing unit to display the OCT data in the image frame on the display such that the first portion of the OCT data is displayed at the depth level in the image frame set based on the line length of the B-scan, based on association between line lengths of B-scans and depth levels, and based on the predetermined ocular parameter value including at least one of the axial length and the optical power; and
setting the line lengths of the B-scans and the depth levels in the association such that the depth levels increase as the line lengths become longer.

26. A computer-readable non-transitory recording medium storing a program configured to cause a computer to execute steps comprising:
controlling an ophthalmic apparatus that includes a display, an interferometer, an optical path length changing unit including an actuator, and a processor and applies OCT to an eye, the interferometer including a measurement arm and a reference arm, the optical path length changing unit being configured to change at least one of an optical path length of the measurement arm and an optical path length of the reference arm;
controlling the processor to generate OCT data based on an output from the interferometer;
controlling the optical path length changing unit to display the OCT data in an image frame on the display such that a first portion of the OCT data corresponding to a predetermined part of the eye is displayed at a depth level in the image frame set based on a line length of a B-scan in the OCT data and based on a predetermined ocular parameter value including at least one of an axial length and an optical power;
controlling the optical path length changing unit to display the OCT data in the image frame on the display such that the first portion of the OCT data is displayed at the depth level in the image frame set based on the line length of the B-scan, based on association between line lengths of B-scans and depth levels, and based on the predetermined ocular parameter value including at least one of the axial length and the optical power; and
setting the line lengths of the B-scans and the depth levels in the association such that the depth levels increase as the line lengths become longer.

* * * * *